(12) United States Patent
Konstorum et al.

(10) Patent No.: US 10,028,644 B2
(45) Date of Patent: Jul. 24, 2018

(54) OBLONG ENDOSCOPE SHEATH

(71) Applicant: Gyrus ACMI, Inc., Southborough, MA (US)

(72) Inventors: Gregory S. Konstorum, Stamford, CT (US); Ming J. Cheng, W. Warwick, RI (US); Daniel R. Goldberg, Memphis, TN (US)

(73) Assignee: GYRUS ACMI, INC., Southborough, MA (US)

( * ) Notice: Subject to any disclaimer, the term of this patent is extended or adjusted under 35 U.S.C. 154(b) by 60 days.

(21) Appl. No.: 14/496,473

(22) Filed: Sep. 25, 2014

(65) Prior Publication Data
US 2015/0087907 A1 Mar. 26, 2015

Related U.S. Application Data

(60) Provisional application No. 61/882,652, filed on Sep. 26, 2013.

(51) Int. Cl.
*A61B 1/04* (2006.01)
*A61B 1/015* (2006.01)
(Continued)

(52) U.S. Cl.
CPC .......... *A61B 1/015* (2013.01); *A61B 1/00068* (2013.01); *A61B 1/00119* (2013.01);
(Continued)

(58) Field of Classification Search
CPC .. A61B 1/126; A61B 1/00135; A61B 1/00119
(Continued)

(56) References Cited

U.S. PATENT DOCUMENTS 1,555,003 A * 9/1925 Greenberg ......... A61B 1/00135
600/117
2,112,056 A * 3/1938 Wappler ............ A61B 1/00135
600/153
(Continued)

FOREIGN PATENT DOCUMENTS

EP 0374727 A1 6/1990
JP H05/038323 A 2/1993
(Continued)

OTHER PUBLICATIONS

US 5,772,579, 06/1998, Reisdorf (withdrawn)
(Continued)

*Primary Examiner* — Anhtuan T Nguyen
*Assistant Examiner* — Jae Woo
(74) *Attorney, Agent, or Firm* — The Dobrusin Law Firm P.C.

(57) ABSTRACT

An endoscope sheath comprising: a proximal end; a distal end having a distal end region; a surface extending between and connecting the proximal end and the distal end; and a plurality of positioning devices located along the surface; wherein the sheath is configured to: (1) receive all or a portion of an endoscope having a cylindrical end and (2) provide a conduit for communicating fluid between the proximal end of the sheath and the distal end of the sheath when the endoscope is inserted inside the sheath; and wherein the distal end region of the sheath includes the plurality of positioning devices that secure the cylindrical end of the endoscope against a portion of an inner wall of the surface extending between the proximal end and the distal end so that a fluid barrier is created between the cylindrical end of the endoscope and the inner wall.

3 Claims, 13 Drawing Sheets

(51) Int. Cl.
   *A61B 1/00*      (2006.01)
   *A61B 1/06*      (2006.01)
   *A61B 1/12*      (2006.01)
   *A61B 90/70*     (2016.01)

(52) U.S. Cl.
   CPC ...... *A61B 1/00135* (2013.01); *A61B 1/00142*
       (2013.01); *A61B 1/06* (2013.01); *A61B 1/126*
         (2013.01); *A61B 90/70* (2016.02); *A61B*
         *1/00128* (2013.01); *A61B 2090/701* (2016.02)

(58) Field of Classification Search
   USPC .................. 600/157, 156, 123, 121, 125
   See application file for complete search history.

(56) References Cited

U.S. PATENT DOCUMENTS

| | | | |
|---|---|---|---|
| 4,254,762 A | | 3/1981 | Yoon |
| 4,281,646 A | | 8/1981 | Kinoshita |
| 4,312,375 A | | 1/1982 | Leinemann |
| 4,548,197 A | | 10/1985 | Kinoshita |
| 4,646,722 A | | 3/1987 | Silverstein et al. |
| 4,850,342 A | * | 7/1989 | Hashiguchi ........ A61B 1/00179 600/171 |
| 4,991,565 A | * | 2/1991 | Takahashi .......... A61B 1/00142 600/123 |
| 5,167,220 A | * | 12/1992 | Brown ................. A61B 1/12 600/156 |
| 5,170,774 A | | 12/1992 | Heckele |
| 5,176,645 A | | 1/1993 | Guerrero |
| 5,178,606 A | | 1/1993 | Ognier et al. |
| 5,199,417 A | | 4/1993 | Muller et al. |
| 5,207,213 A | | 5/1993 | Auhll et al. |
| 5,237,984 A | | 8/1993 | Williams et al. |
| 5,269,756 A | | 12/1993 | Dryden |
| 5,313,934 A | * | 5/1994 | Wiita ................. A61B 1/00091 600/109 |
| 5,354,267 A | | 10/1994 | Niermann et al. |
| 5,413,092 A | | 5/1995 | Williams, III et al. |
| 5,419,309 A | | 5/1995 | Biehl |
| 5,439,022 A | | 8/1995 | Summers et al. |
| 5,486,155 A | | 1/1996 | Muller et al. |
| 5,505,707 A | | 4/1996 | Manzie et al. |
| 5,551,448 A | | 9/1996 | Matula et al. |
| 5,554,100 A | * | 9/1996 | Leiner ................. A61B 1/00179 385/117 |
| 5,554,112 A | | 9/1996 | Walbrink et al. |
| 5,556,258 A | | 9/1996 | Lange et al. |
| 5,575,756 A | * | 11/1996 | Karasawa .......... A61B 1/00068 600/121 |
| 5,630,795 A | | 5/1997 | Kuramoto et al. |
| 5,647,840 A | * | 7/1997 | D'Amelio .......... A61B 1/00091 600/169 |
| 5,681,262 A | * | 10/1997 | Isse .................. A61B 1/012 600/104 |
| 5,700,236 A | * | 12/1997 | Sauer ................. A61B 1/00101 600/121 |
| 5,779,625 A | * | 7/1998 | Suzuki .............. A61B 1/00057 600/121 |
| 5,785,689 A | * | 7/1998 | de Toledo .......... A61B 17/3478 604/158 |
| 5,797,836 A | | 8/1998 | Lucey et al. |
| 5,823,940 A | * | 10/1998 | Newman ............ A61B 1/00091 600/105 |
| 5,989,183 A | | 11/1999 | Reisdorf et al. |
| 6,110,103 A | | 4/2000 | Donofrio |
| 6,126,592 A | * | 10/2000 | Proch ................. A61B 1/00091 600/114 |
| 6,181,442 B1 | | 1/2001 | Ogura et al. |
| 6,196,967 B1 | * | 3/2001 | Lim .................. A61B 1/00128 600/125 |
| 6,282,442 B1 | | 8/2001 | DeStefano et al. |
| 6,354,813 B1 | | 3/2002 | Laing |
| 6,447,446 B1 | * | 9/2002 | Smith ................ A61B 1/00142 600/118 |
| 6,478,731 B2 | | 11/2002 | Speier et al. |
| 6,558,379 B1 | | 5/2003 | Batchelor et al. |
| 6,652,484 B1 | | 11/2003 | Hunckler et al. |
| 7,160,247 B2 | * | 1/2007 | Deppmeier ............ A61B 1/002 600/129 |
| 7,252,110 B2 | | 8/2007 | Semeia |
| 7,270,647 B2 | | 9/2007 | Karpowicz et al. |
| 7,413,542 B2 | | 8/2008 | Kucklick et al. |
| 7,708,689 B2 | | 5/2010 | Deppmeier et al. |
| 7,766,819 B2 | * | 8/2010 | Matsumoto ........ A61B 1/00089 600/128 |
| 7,811,228 B2 | | 10/2010 | Adams |
| 8,001,984 B2 | | 8/2011 | Sasaki |
| 8,029,438 B2 | * | 10/2011 | Hagihara ........... A61B 1/00071 600/127 |
| 8,047,215 B1 | | 11/2011 | Sasaki |
| 8,079,952 B2 | | 12/2011 | Fujimoto |
| 8,231,574 B2 | | 7/2012 | Haack et al. |
| 8,337,470 B2 | | 12/2012 | Prasad et al. |
| 8,393,328 B2 | * | 3/2013 | Angel .................... A61M 16/04 128/200.26 |
| 8,394,013 B2 | | 3/2013 | Ichimura |
| 8,409,109 B2 | * | 4/2013 | Tiesma .................... A61B 5/01 600/115 |
| 8,419,624 B2 | | 4/2013 | James et al. |
| 8,911,415 B2 | * | 12/2014 | Knapp ............... A61B 1/307 604/264 |
| 9,155,453 B2 | * | 10/2015 | Kumar ............... A61B 1/00071 |
| 2001/0000041 A1 | * | 3/2001 | Selmon .............. A61B 17/3207 600/585 |
| 2002/0120180 A1 | | 8/2002 | Speier et al. |
| 2004/0073088 A1 | | 4/2004 | Friedman et al. |
| 2005/0025646 A1 | | 2/2005 | Miller et al. |
| 2005/0267330 A1 | * | 12/2005 | Deppmeier ............ A61B 1/04 600/114 |
| 2006/0020165 A1 | * | 1/2006 | Adams ............... A61B 1/00094 600/121 |
| 2006/0041186 A1 | * | 2/2006 | Vancaillie .......... A61B 1/00071 600/128 |
| 2006/0199998 A1 | | 9/2006 | Akui et al. |
| 2006/0264995 A1 | | 11/2006 | Fanton et al. |
| 2007/0213668 A1 | | 9/2007 | Spitz |
| 2008/0045859 A1 | * | 2/2008 | Fritsch ............... A61B 17/3417 600/567 |
| 2008/0072970 A1 | | 3/2008 | Gasser et al. |
| 2008/0081948 A1 | | 4/2008 | Weisenburgh et al. |
| 2008/0200764 A1 | | 8/2008 | Okada |
| 2008/0242935 A1 | * | 10/2008 | Inoue ................. A61B 1/00096 600/176 |
| 2008/0262308 A1 | * | 10/2008 | Prestezog ............. A61B 1/015 600/123 |
| 2009/0234193 A1 | | 9/2009 | Weisenburgh, II et al. |
| 2009/0244223 A1 | | 10/2009 | Mizutani et al. |
| 2010/0198012 A1 | | 8/2010 | Poole et al. |
| 2011/0230716 A1 | | 9/2011 | Fujimoto |
| 2011/0295066 A1 | * | 12/2011 | Fan .................... A61B 1/00119 600/114 |
| 2012/0178995 A1 | * | 7/2012 | Newton, IV ........ A61B 1/00101 600/121 |
| 2012/0316394 A1 | | 12/2012 | Yoshida et al. |
| 2013/0205936 A1 | | 8/2013 | Schmieding et al. |
| 2013/0211433 A1 | | 8/2013 | Kadykowski et al. |
| 2013/0217970 A1 | | 8/2013 | Weisenburgh, II .... A61B 1/126 600/157 |
| 2013/0289595 A1 | | 10/2013 | Edwards et al. |
| 2014/0364871 A1 | * | 12/2014 | Kucklick ............ A61M 1/0084 606/130 |
| 2015/0045678 A1 | * | 2/2015 | Ohzawa ............... A61B 5/0084 600/478 |
| 2015/0182108 A1 | * | 7/2015 | Fukuda ............... A61B 1/00135 600/157 |

(56) References Cited

U.S. PATENT DOCUMENTS

| | | | |
|---|---|---|---|
| 2015/0282695 A1* | 10/2015 | Tay | A61B 1/00135 600/124 |
| 2016/0089006 A1* | 3/2016 | Poll | A61B 1/00119 600/560 |
| 2016/0095510 A1* | 4/2016 | Oskin | A61B 1/307 600/109 |

FOREIGN PATENT DOCUMENTS

| | | |
|---|---|---|
| JP | H06/189893 A | 7/1994 |
| JP | H07-308286 | 11/1995 |
| JP | 2005/040184 A | 2/2005 |
| JP | 2012/045325 A | 3/2012 |
| WO | 2002/032296 A2 | 4/2002 |
| WO | 2012/069592 A1 | 5/2012 |

OTHER PUBLICATIONS

Potentially Related Application, U.S. Appl. No. 14/497,815, filed Sep. 26, 2014.
Potentially Related Application, U.S. Appl. No. 14/493,581, filed Sep. 23, 2014.
Potentially Related Application, U.S. Appl. No. 14/493,700, filed Sep. 23, 2014.
Potentially Related Application, U.S. Appl. No. 14/551,208, filed Nov. 24, 2014.
Potentially Related Application, U.S. Appl. No. 14/551,440, filed Nov. 24, 2014.
Japanese Office Action dated Jan. 31, 2017 for Application No. 2016-537952.
State Intellectual Property Office of China Office Action for Application No. 201480047065.X dated Feb. 28, 2017.
Japanese Office Action for Japanese Patent Application No. 2016-537952; dated Oct. 3, 2017.
State Intellectual Property Office of China Office Action for Application No. 201480047065.X dated Mar. 13, 2018.

* cited by examiner

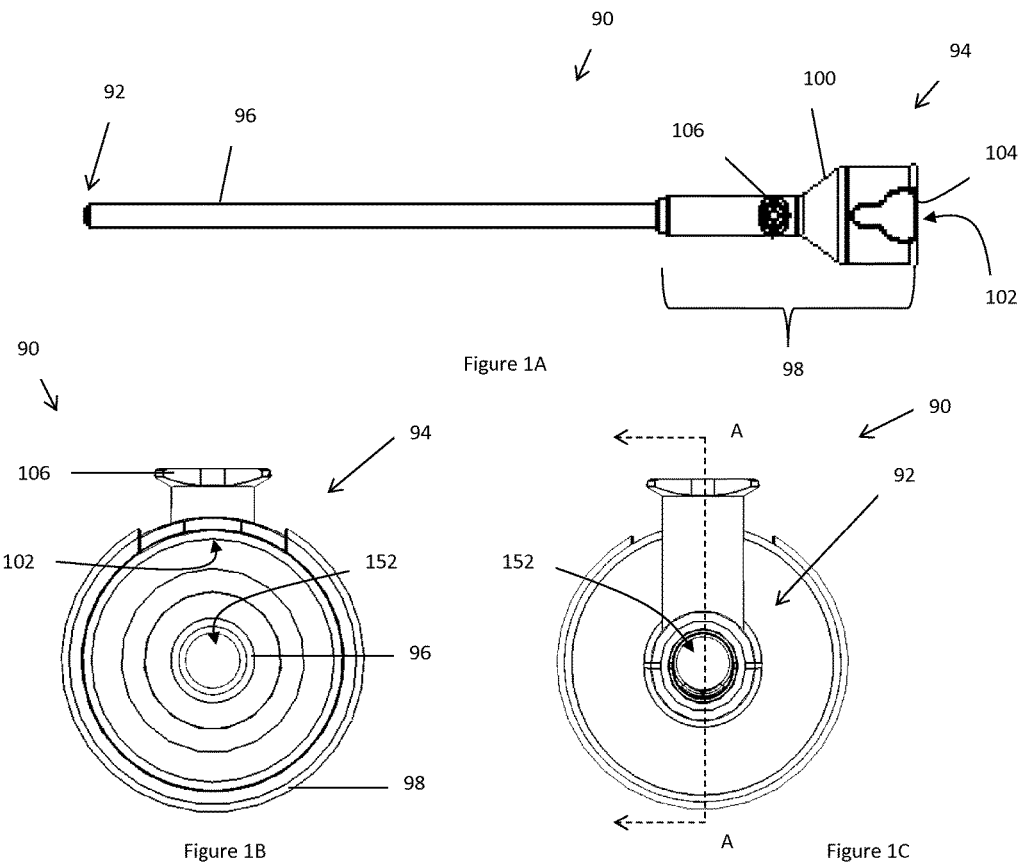
Figure 1A
Figure 1B
Figure 1C
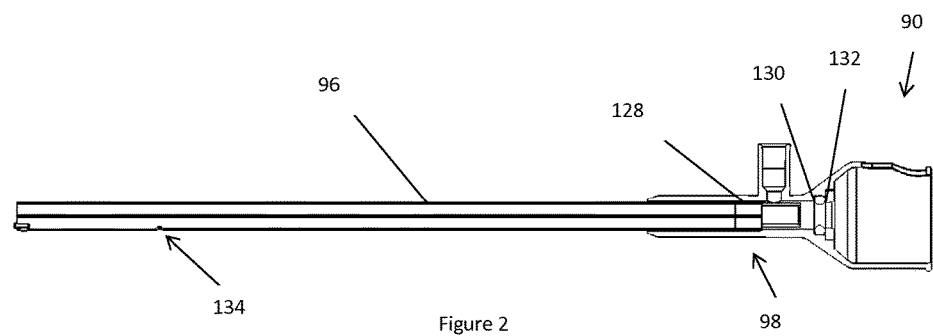
Figure 2

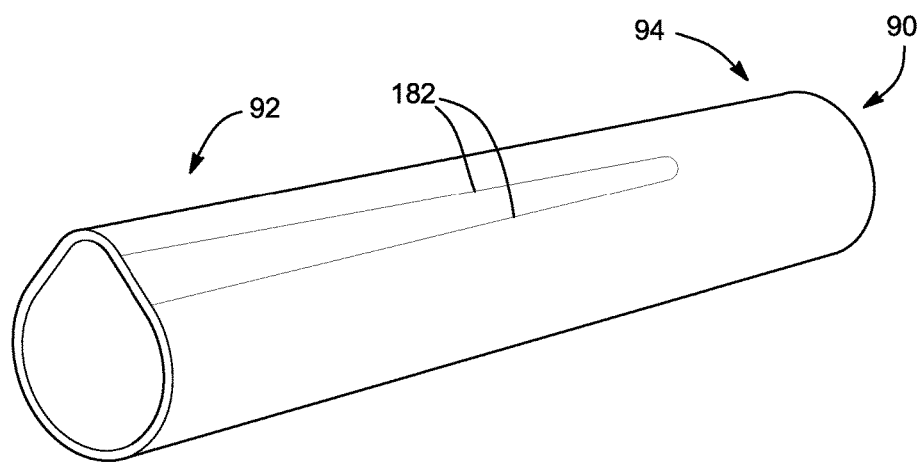
Figure 5A
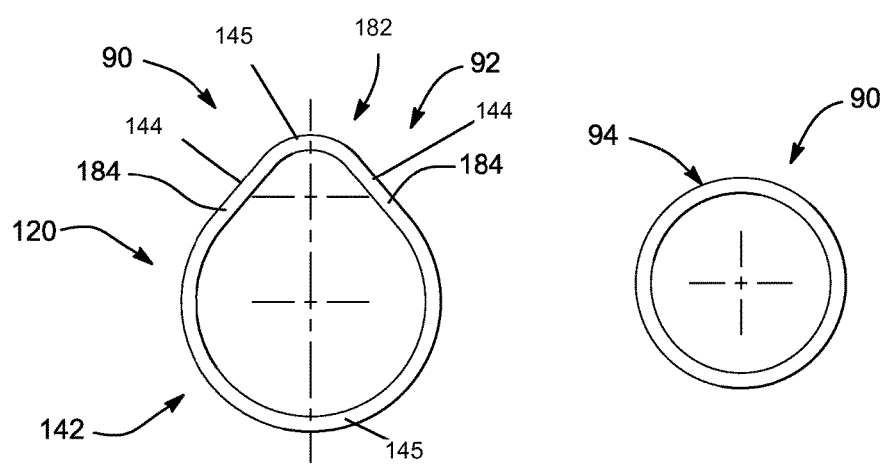 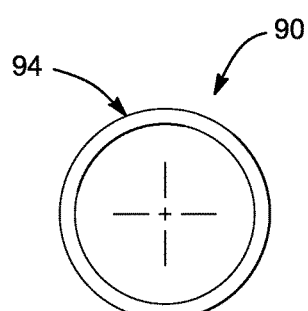
Figure 5B            Figure 5C

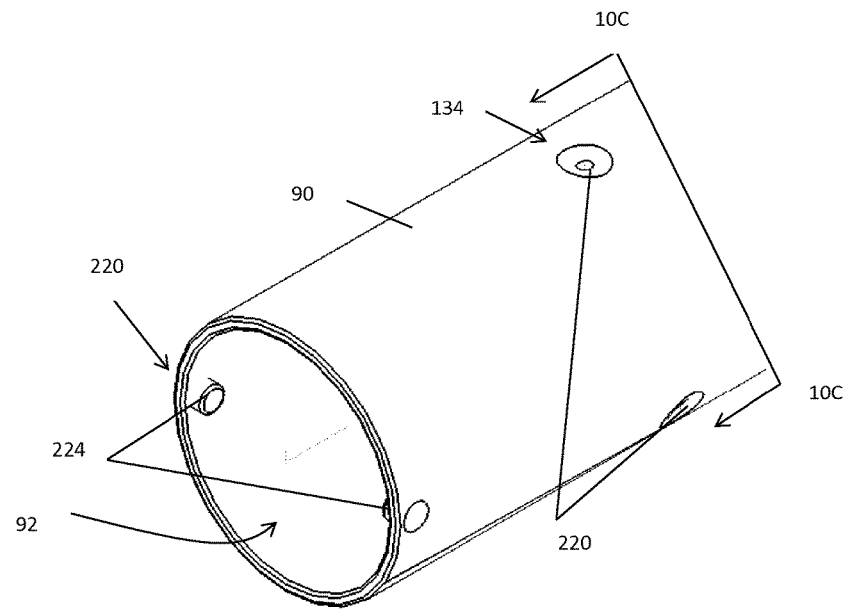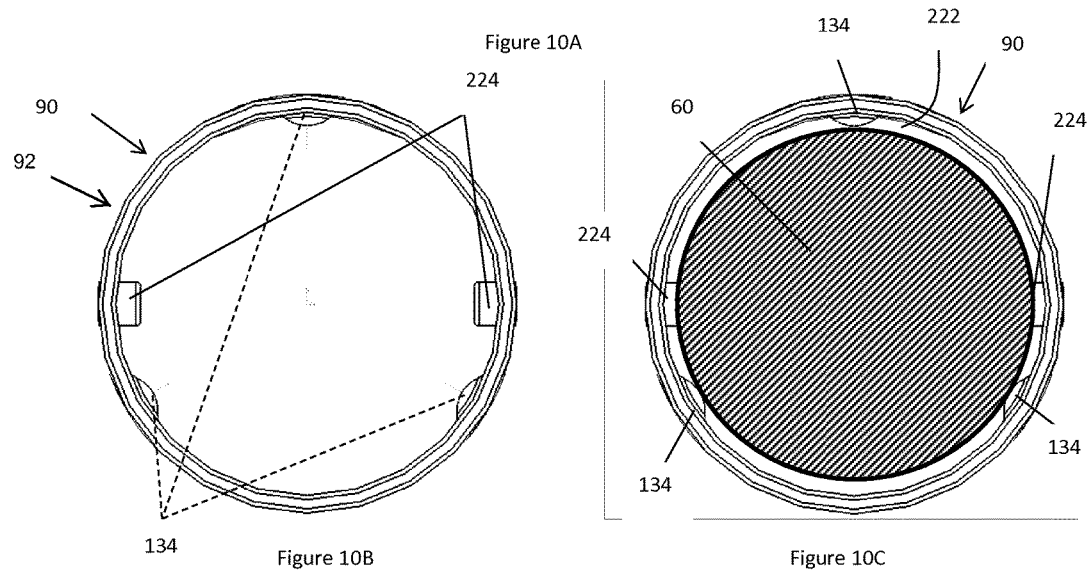
Figure 10A
Figure 10B
Figure 10C

OBLONG ENDOSCOPE SHEATH

FIELD

The present teachings generally relate to an endoscope sheath that receives all or a portion of an endoscope and more specifically to an endoscope sheath that self-aligns the endoscope within the sheath creating a channel, lumen, or both.

BACKGROUND

Endoscopes are typically used for minimally invasive surgery or to provide access to an internal location of a patient so that a doctor is provided with visual access. Endoscopes, during use, may be inserted into a location that may include debris that may cover the end of the endoscope and especially cover an imaging device located at the end of the endoscope. For example, an endoscope being used for surgery may become covered by blood and the blood may impair the vision of a surgeon so that surgery becomes increasingly difficult. Attempts have been made to provide various devices to assist a surgeon in clearing the debris from the imaging device of the endoscope and restore vision. These devices may remove some of the debris from the imaging device of the endoscope, however, these devices may not remove all of the debris and/or may leave spots or droplets on the imaging device, which may result in continued impairment. These devices may have features that attempt to control the flow of fluid, suction, or both at the end of the endoscope in an attempt to clear debris, spots, droplets, or a combination thereof from the endoscope. Further, many of the features at the end of the sheath are configured to align the sheath with the endoscope and these feature perform little if any directing of fluid across the end of the endoscope.

Examples of some endoscope cleaning devices may be found in U.S. Pat. Nos. 5,575,756; 7,708,689; and 8,079,952; and U.S. Patent Application Publication No. 2011/0230716. all of which are incorporated by reference in their entirety herein for all purposes. It would be attractive to have an endoscope sheath that self-aligns the endoscope within the sheath so that a conduit, a lumen, a channel, or a combination thereof is created along all or a portion of the length of the sheath. It would be attractive to have an endoscope sheath that includes a channel that can accommodate fluid, suction, one or more functional elements, or a combination thereof. What is needed is an endoscope sheath that includes one or more non-circular sections that align the endoscope within the sheath and create a channel, conduit, a lumen, or a combination thereof.

SUMMARY

The present teachings meet one or more of the present needs by providing: an endoscope sheath comprising: a proximal end; a distal end having a distal end region; a surface extending between and connecting the proximal end and the distal end; and a plurality of positioning devices located along the surface; wherein the sheath is configured to: (1) receive all or a portion of an endoscope having a cylindrical end and (2) provide a conduit for communicating fluid between the proximal end of the sheath and the distal end of the sheath when the endoscope is inserted inside the sheath; and wherein the distal end region of the sheath includes the plurality of positioning devices that secure the cylindrical end of the endoscope against a portion of an inner wall of the surface extending between the proximal end and the distal end so that a fluid barrier is created between the cylindrical end of the endoscope and the inner wall.

Another possible embodiment of the present teachings comprises: an endoscope cleaner comprising: a sheath having: a proximal end, a distal end, and an inner surface extending between the proximal end and the distal end; wherein the sheath is configured to receive all or a portion of an endoscope and provide a conduit for communicating fluid between the proximal end of the sheath and the distal end of the sheath when the endoscope is inserted inside the sheath, and wherein the distal end of the sheath has a cross-section with a circular portion having a diameter substantially matching a diameter of the endoscope and one or more tangent portions that have one or more segments that are tangent to the circular portion at one or more points.

Yet another possible embodiment of the present teachings provides: an endoscope cleaner comprising: (a) a proximal end, (b) a distal end including: (i) two or more non-unitary positioning features that are configured to provide an axial end stop for an endoscope, and (c) a surface extending between and connecting the proximal end and the distal end, wherein the two or more non-unitary positioning features are connected to the distal end of the surface by one or more fasteners, adhesives, or both.

The teachings herein provide an endoscope sheath that self-aligns the endoscope within the sheath so that a conduit, a lumen, a channel, or a combination thereof is created along all or a portion of the length of the sheath. The teachings herein provide an endoscope sheath that includes a channel that can accommodate fluid, suction, one or more functional elements, or a combination thereof. The teachings herein provide an endoscope sheath that includes one or more non-circular sections that align the endoscope within the sheath and create a channel, conduit, a lumen, or a combination thereof.

BRIEF DESCRIPTION OF THE DRAWINGS

FIG. 1A illustrates a top view of an endoscope sheath;

FIG. 1B illustrates a proximal end view of an endoscope sheath of FIG. 1A;

FIG. 1C illustrates a distal end view of an endoscope sheath of FIG. 1A;

FIG. 2 illustrates a cross sectional view of FIG. 1C along lines A-A;

FIG. 5A illustrates a side view of a sheath having a non-circular perimeter along a portion of the length;

FIG. 58B illustrates a distal end view of the sheath of FIG. 5A;

FIG. 5C illustrates a proximal end view of the sheath of FIG. 5A;

FIG. 10A illustrates a perspective view of a sheath having a plurality of positioning devices that are off set;

FIG. 10B illustrates an end view of the sheath of FIG. 10A;

FIG. 10C illustrates a view of the proximal end side of the endoscope of FIG. 10A;

DETAILED DESCRIPTION

Figure 3A:
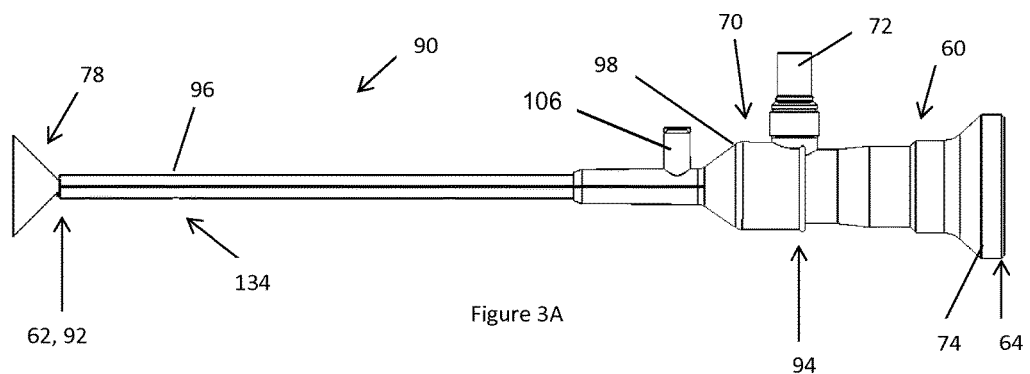
FIG. 3A illustrates a side view of an endoscope inserted in the endoscope sheath of FIG. 1A.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present application claims priority to U.S. Provisional Patent Application Ser. No. 61/882,652, filed on Sep. 26, 2013, the contents of which are incorporated by reference herein in their entirety for all reasons. The present teachings provide an endoscope sheath 90 for use in a system 2. The system 2 of the teachings herein includes an irrigation source 4 and a suction source 10 that are both connected to an endoscope sheath 90 that is in communication with an endoscope 60. The system 2 may include one or more control modules 30. The system 2 may function to clean an endoscope 60. Preferably, the system 2 functions to clean a distal tip 62 of an endoscope 60. More preferably, the system 2 functions to clean an imaging device of an endoscope 60. The system 2 may include one or more functional components that may extend proximate to a distal end 62 of an endoscope 60 or beyond a distal end of an endoscope. The system 2 may provide one or more conduits relative to the endoscope 60. The system 2 may protect the endoscope 60.

The system 2 may include one or more sources of irrigation fluid 4 for use with the system 2, and the one or more sources of irrigation fluid 4, suction 10, or both may be controlled by one or more control modules 30.

The one or more control modules 30 may function to control the amount of fluid, suction, or both applied to a predetermined area, an area of interest, the endoscope 60, or a combination thereof. The one or more control modules 30 may be powered by electricity, battery powered, or both. The one or more control modules 30 may include one or more pumps 14, one or more valves 8, one or more user interfaces 31, or a combination thereof. The one or more user interfaces 31 may be one or more control knobs, one or more selectors, one or more indicators, one or more user controls, one or more devices for changing a parameter, or a combination thereof. The one or more control modules 30 may include any of the pumps 14 discussed herein and based upon feedback from the user interface 31 may control the pump 14 to perform the selected parameter. The control module 30 may include a microprocessor, a computer, a control algorithm, or a combination thereof. The control module 30 may control one more valves 8 located within the system 2, connected to the control module 30, or both. The one or more control modules 30 may perform a suction function, an irrigation function, or a combination of both upon a selection by the user as is indicated by the user interface 31. The control module 30 may control the running speed, pumping duration, or both of the pump so that irrigation fluid is moved to the sheath 90.

The irrigation fluid may function to clean an endoscope 60, clear debris from a location proximate to the endoscope, be bioabsorbable, or a combination thereof. The irrigation fluid may function to move solid particles, move opaque fluids, or both. The irrigation fluid may be applied with a pressure. The pressure of the irrigation fluid may be varied by changing the height of the irrigation source 4 relative to the sheath 90 so that the head of the irrigation fluid is increased or decreased. The pressure of the irrigation fluid may be sufficiently high so that the irrigation fluid may be redirected by a flow director. The irrigation fluid may be applied with a pressure of about 0.10 MPa or more, about 0.20 MPa or more, about 0.30 MPa or more, or even about 0.50 MPa or more. The irrigation fluid may be applied with a pressure of about 3 MPa or less, about 2 MPa or less, about 1 MPa or less, or even about 0.75 MPa or less. The irrigation fluid may be applied with a sufficient amount of pressure that the surface tension of the irrigation fluid wicks the irrigation fluid across the distal end 62, the imaging portion, or both of the endoscope 60 (e.g., the pressure may be low enough that the irrigation fluid remains in contact with the endoscope 60, the sheath 90, or both). The irrigation fluid may be applied with a gravity feed, thus, the pressure of the irrigation fluid may be determined by the height of an irrigation source. For example, the irrigation source 4 may be an IV bag and the height of the IV bag may determine the amount of pressure and/or force generated at the distal tip of the sheath 92, endoscope 62, or both. The irrigation fluid may be applied by a pump 14 that pumps the fluid at a predetermined pressure. The irrigation fluid may be continuously applied, intermittently applied, or both during an application cycle. The pressure of the irrigation fluid may change when the irrigation fluid reaches the end of an endoscope sheath 90 so that the fluid cleans the endoscope 60, creates turbulence at the end of the endoscope, or both. Preferably, the pressure is sufficiently low so that the flow across the endoscope 60 is laminar. The pressure of the irrigation fluid may be varied based upon the size, length, or both of an irrigation line 6 extending between an irrigation source 4 and the sheath 90. The irrigation source 4 may be a reservoir that fluid is drawn from by a fluid movement mechanism (e.g., a pump 14) and moved through the sheath 90 to provide irrigation to a distal end of an endoscope 62, to clean an endoscope 60, or both.

The pump 14 may function to circulate irrigation fluid, move irrigation fluid through one or more lines 6, move fluid through a sheath 90, or a combination thereof. The pump 14 may function to create a negative pressure (e.g., suction or vacuum). The pump 14 may move fluid with an impeller. The pump 14 may be a lobe pump, a centrifugal pump, a positive displacement pump, a rotary positive displacement pump, a diaphragm pump, peristaltic pump, rope pump, a gear pump, a screw pump, a progressing cavity pump, a roots-type pump, a plunger pump, or a combination thereof. Preferably, the pump 14 moves a constant amount of fluid upon being activated, a constant amount of fluid may be varied from application to application, or both. More preferably, the pump 14 is a peristaltic pump.

The one or more irrigation lines 6 may function to connect the sheath 90 to an irrigation source 4. The irrigation lines 6 may function to create a head so that pressure is created and the irrigation fluid is applied with a force. The irrigation line 6 may be flexible, movable, or both. The irrigation line 6 may be made of any material that is compatible with the irrigation fluid, a patient, use in a surgical procedure, or a combination thereof. The irrigation line 6 may connect the sheath 90 to an irrigation source 4, a suction source 10, or both (i.e., suction may be applied through the irrigation line 6).

The suction source 10 may function to remove fluid, debris, opaque fluids, unwanted material, or a combination thereof from a point of interest, from a distal end of the sheath 92, a distal end of the endoscope 62, or a combination thereof. The suction source 10 may function to perform a drying function, remove fluid spots, or both. The suction source 10 may be a pump, reversal of a motor, a common suction source, a hospital suction source, or a combination thereof. The suction source 10 may apply a sufficient amount of vacuum to remove a predetermined amount of fluid in a predetermined amount of time. For example, the suction source 10 may apply suction so that 10 ml of fluid may be removed in 1 to 2 seconds. The suction source may apply a continuous suction, intermittent suction, or both.

The suction line 12 may function to connect to the sheath 90 so that suction may be pulled through the sheath 90. The suction line 12 may function to connect the sheath 90 to a suction source 10. The suction line 12 may assist is moving fluids, removing fluids, removing debris, removing opaque fluids, removing particles, or a combination thereof. The suction line 12 may be any line that may assist in creating a vacuum at a distal tip of the endoscope 62, the sheath 92, or both. The suction line 12 and the irrigation line 6 may be the same line. The suction line 12 and the irrigation line 6 may be connected to a common line 18. The suction line 12 and the irrigation line 6 may be connected by one or more fittings 16, one or more valves 8 or both.

The one or more valves 8 may function to allow only one functions (e.g., irrigation or suction) to work at a time. The one or more valves 8 may function to block the irrigation line 6, the suction line 12, or both. The one or more valves 8 may only allow suction or irrigation to be applied at a given time. The one or more valves 8 may be or include a check valve, a back flow preventer, or both. The one or more valves 8 may be located proximate to the sheath 90, proximate to the irrigation source 10, proximate to the suction source 4, or a location therebetween. Each of the lines may include a valve 8. If more than one valve is present the valves may be electrically connected, hydraulically connected, fluidly connected, or a combination thereof so that if one valve is opened another valve is closed. The two or more valves (e.g., a first valve and a second valve) may be electrically connected, electrically controlled, or both. The two or more valves may be operated in a sequence (e.g., one opened and then one dosed), operated simultaneously, operated on a delay, or a combination thereof. For example, only one valve may be open at a time. In another example, one may close and after a time delay another may open. The one or more valves 8 may be part of a common fitting 16, located proximate to a common fitting, or both.

The one or more common fittings 16 may function to connect two or more lines into a common line 18. The one or more common fittings 16 may function to connect a suction line 12 and an irrigation line 6 to a common port. The one or more common fittings 16 may connect a single line to multiple devices so that multiple devices may be used simultaneously, in series, in parallel, or a combination thereof. For example, the common fitting 16 may connect a suction line 12 and an irrigation line 6 to a common line 18 that is connected to a sheath 90 and, during operation, an irrigation fluid may be applied and then after a delay and/or immediately when the irrigation fluid ceases to be applied, suction may be applied to the suction line 12 so that irrigation fluid, excess irrigation fluid, debris, particles, opaque fluids, or a combination thereof are removed from the distal end of the endoscope 62. The one or more common fittings 16 may have two or more openings, three or more openings, four or more openings, or even five or more openings. Each opening may receive at least one line and fluidly connect the one or more lines together. More than one common fitting 16 may be used to connect multiple lines together. For example, a first common fitting with three openings may be connected to second common fitting with three openings so that two tubes are connected to one opening of the first common fitting and one tube is connected to each of the other two openings. Preferably, the common fitting 16 is generally "Y" shaped and two of the openings lead into a third opening that is connected to a common line 18 and/or a delivery line 42.

The common line 18 may function to deliver irrigation fluid, suction, or both to a sheath 90. The common line 18 may function to provide a combination of multiple different fluids, devices, suction levels, fluid pressures, or a combination thereof. The common line 18 may provide a single access point between the irrigation source 4, the suction source 10, or both and the sheath 90. The common line 18 may have an increased cross-sectional area (e.g., diameter) relative to the cross-sectional area of the irrigation line 6, the suction line 12, or both. The common line 18 may be the same size as one or both of the irrigation line 6, the suction line 12, or both. The common line 18 may extend between the common fitting 16 and a port of the sheath 106. The common line 18 may be a delivery line 42.

The delivery line 42 may function to deliver fluids to a sheath 90. The delivery line 42 may function to deliver suction to the sheath 90. The delivery line 42 and the common line 18 are preferably the same line. The delivery line 42, common line 18, or both may be used during an application cycle.

The application cycle may be any cycle where an endoscope 60 is cleaned. The application cycle may be a cycle where a combination of different items are applied, a combination of different sequences are performed, or both. The application cycle may be a cycle where an irrigation fluid and suction are applied in a sequence to clean an endoscope 60. The application cycle may be a combination of one or more applications of fluid, one or more applications of suction, or both. The application cycle may be an application of fluid and immediately thereafter an application of suction to remove excess fluid form a point of interest, the distal end of the endoscope 62, the distal end of the sheath 92, or a combination thereof. The application cycle may have no delay between an end of the application of an irrigation fluid and the beginning of the application of suction. For example, upon completion of the irrigation fluid being applied the suction may immediately begin. The application cycle may be varied by a user. The application cycle may include only an application of fluid (i.e., a flushing cycle, a washing manner) with no suction. The application cycle may be user activated for a predetermined amount of time. The application cycle may be activated based upon a duration a user activates a switch. For example, a user may pre-set the activation cycle so that one touch of the switch causes the irrigation fluid to run for 5 seconds. The user may pre-set the activation cycle so that no suction is used. The application cycle may concurrent application of fluid and suction. For example, suction may begin being applied before the irrigation fluid is turned off. The application cycle of the irrigation fluid, the suction, or both may be changed by a user changing a selector, actuating a control longer, changing an input, or a combination thereof. The application cycle may be sufficiently long so that an image sensor of an endoscope 60 is clear and good images may be taken.

The endoscope 60 may function to provide an image to a surgeon, a doctor, a nurse, any other person who desires visual access to a remote location, or a combination thereof. The endoscope 60 may be used for non-invasive surgery. The endoscope 60 may be used for orthoscopic surgery. The endoscope 60 may be inserted in a cut in tissue. The endoscope 60 may be used for insertion into an orifice including an ear, nose, throat, rectum, or a urethra. The endoscope 60 may have a generally circular cross-section. The endoscope may have a tubular section that is generally cylindrical (i.e., internal portion). The endoscope may have a tubular section extending to the distal end 62 and a handpiece connected to the tube and extending to the proximal end 64. The endoscope 60 may have a cylindrical distal end 62. The body of the endoscope 60 and the distal end 62 of the endoscope may be different shapes. The endoscope 60 may include one or more image sensors in a distal end region (i.e., internal portion). The one or more image sensors may be located in an external portion of the endoscope 60 and fiber optics connected to the image sensor may transmit a signal through the internal portion to the external portion. The endoscope 60 may include two or more image sensors. The endoscope 60 may include an image sensor at the most distal point of the endoscope 60. The endoscope 60 may include an image sensor that is located on an angle. The angle of the image sensor, viewing face, or both may be about 0°, 20°, 30°, 45°, 60°, 70°, or a combination thereof. The image sensor may provide black and white images, color images, thermal images, or a combination thereof. Preferably, the image sensor, imaging device, or both are located substantially at the distal end 62. The angle of the image sensor, the viewing face, or both may dictate the angle, shape, viewing cone 78, or a combination thereof of the endoscope 60.

The viewing cone 78 may be an area of visibility of the endoscope 78. The viewing cone 78 may be variable, adjustable, or both. The angle of the viewing cone 78 may be movable. The angle of the viewing cone 78 may be predetermined based upon the type of endoscope 60 selected. The angle of the viewing cone 78 may not be affected by the flow director, lumen, sheath 90, or a combination thereof. The location of the endoscope 60 within the sheath 90 may vary based upon the angle of the viewing cone 78. For example, the shape of the sheath 90 may offset the endoscope 60 to one side more or less based upon the angle of the viewing cone 78 so that the endoscope sheath 90 does not interfere with the imaging of the endoscope 60. The viewing cone 78 may extend outward from the distal end 62 of the endoscope in a cone shape.

The distal end 62 of the endoscope 60 may function to be inserted into a patient so that a feature of interest may be viewed through minimally invasive means. The distal end 62 of the endoscope 60 may be the leading portion of the endoscope (i.e., the first portion that enters a patient). The distal end 62 may function to provide washing functions, suction functions, irrigating functions, or a combination thereof that direct the irrigation fluid and suction across the viewing face of the endoscope 60, the lens, or both. The distal end 62 may include one or more openings. The one or more openings may be at the very end of the distal end 62 (e.g., a 0 degree opening). The one or more opening may be in a sidewall of the sheath 90, the tube, or both (e.g., 15 degrees, 20 degrees, 30 degrees, 45 degrees, 60 degrees, 70 degrees). The one or more openings may extend into the one or more openings so that a feature of interest may be viewed through the opening. The opening may extend at an angle as the opening extends from the proximal end 64 towards the distal end 62. The opening may extend at a downward angle so that when an angled endoscope is inserted into the sheath 90 the sheath does not interfere with viewing a feature of interest. The distal end 62 of the endoscope 60 may be on an opposing end of the endoscope 60 as a proximal end 64. The proximal end 64 may function to be gripped by a user. The proximal end 64 may function to provide controls to a user. The proximal end 64 may provide an interface for connecting other functional components such as an imaging device (e.g., a camera). The proximal end 64 may function to provide power, sensing, suction, fluid, control, a connection point to outside devices, or a combination thereof to the distal end 62 of the endoscope 60. The proximal end 64 may be retained out of the patient and the distal end 62 may be inserted in the patent. A shoulder 70 may be located between the distal end 62 and the proximal end 64.

The shoulder 70 may function to prevent the proximal end 64 from entering a patient. The shoulder 70 may function to form a connection point with a tube of the endoscope 60. The shoulder 70 may be a terminal portion of a proximal end 64 of the endoscope 60. The shoulder 70 may prevent a sheath 90 from axially moving towards the proximal end 64 of the endoscope 60. The shoulder 70 may be a distal end of the proximal end portion 64 of the endoscope 60. The shoulder 70 may be generally vertical, generally flat, generally orthogonal to the longitudinal axis of the tubular section of the sheath 90, or a combination thereof. One or more light posts 72 may be located in a distal end region of the proximal portion 64 of the endoscope 60 and the light post 72 may be located on a proximal portion of the endoscope 60 relative to the shoulder 70 (e.g., between the shoulder 70 a visual port 74 but closer to the shoulder end then a visual port end).

The light post 72 may function to provide light into the endoscope 60. The light post 72 may direct light into the endoscope 60 and out of the tube of the endoscope 60 so that a feature of interest is illuminated. The light post 72 may provide light so that a user can see features of interests that are located in low light conditions. The light post 72 may be rigid. The light post 72 may be immobile and/or fixedly connected to the endoscope 60 so that the light post 72 has a fixed position on the endoscope 60. The light post 72 may be made of metal, plastic, a biocompatible material, or a combination thereof. The light post 72 may be integral with a main portion of the proximal end 64. The light post 72 may be made of metal and some other biocompatible material. The one or more light posts 72 may provide light through the endoscope 60, so that the visual port may be used for observing a feature of interest at a distal end 62 of the endoscope 60.

The visual port 74 may function to provide a viewing window for a user. The visual port 74 may function to allow a user to observe a feature of interest. The visual port 74 may function to provide an output so that an image is displayed on a monitor. The visual port 74 may provide visual access through the endoscope 60 to a user. The visual port 74 may extend into one or more openings in the sheath 90, a tube of the sheath 96, or both. The angle of the openings discussed herein may be complementary to the angle of the visual port 74 of the endoscope 60. For example, a zero degree endoscope may fit in a zero degree sheath and a 70 degree endoscope may extend into a 70 degree sheath. The visual port 74 may provide a connection point to a camera that displays the image on a larger image device such as a television or a monitor. The visual port 74 may be an optical window at the proximal end 64 that provides visual access to a viewing lens at the distal end.

The viewing lens may function to provide a window that an image sensor views through. The viewing lens may function to protect an image sensor (e.g., a camera). The viewing lens may be a cover over an image sensor. The viewing lens may be a viewing face of the endoscope 60 and vice versa. The viewing face may be a surface of the endoscope 60 that an image is generated through. The viewing lens may have a cross-sectional length (e.g., diameter) that is less than the cross-sectional length of the endoscope 60. The viewing lens may have a largest dimension that is larger than the cross-sectional thickness of the endoscope 60. For example, when the endoscope 60 has an imaging device at a 70° angle the viewing lens may be greater than the cross-sectional length of the endoscope 60. The viewing lens may protect the imaging device (e.g., camera) from fluid, damage, corrosion, or a combination thereof. The viewing lens may cover one or more imaging devices or even two or more imaging devices. The viewing lens when in use may become covered with debris, fluid, blood, opaque fluids, or a combination thereof. The viewing lens may be inhibited from allowing a clear image to be formed. The viewing lens may be partially or fully covered by a sheath 90, be partially or fully surrounded by a sheath 90, or both. Preferably, the sheath 90 is located proximate to the viewing lens without interfering with the range of vision created by the viewing lens.

The sheath 90 may function to provide one or more conduits, lumen, channels, or a combination thereof for a fluid, suction, a functional device (e.g., a cutting tool, cauterizing tool, or both), or a combination thereof to extend out of a distal end 92 region of the sheath 90. The one or more conduits, lumen, channels, or a combination thereof may be a gap between the sheath 90 and the endoscope 60 when viewed in the cross-section. The sheath 90 may function to form all or a portion of a conduit, channel, lumen, or a combination thereof for fluid, suction, a functional device, or a combination thereof to extend out of a distal end 92 region of the sheath 90. The sheath 90 may function to provide cleaning, washing, or both of an endoscope 60. The sheath 90 may provide a conduit, channel, a lumen, or a combination thereof that extends from a proximal end 94 to a distal end 92. The sheath 90 may include one or more lumen, create one or more lumen, or both. The sheath 90 may include one or more parts that when connected together create a conduit that provides irrigation fluid, suction, a functional device, or a combination thereof to a distal end 62 of the endoscope 60. The sheath 90 may substantially mirror the shape of the endoscope 60. Thus, for example, if the endoscope 60 has a circular cross-section then the sheath 90 has a circular cross section 142. Preferably, the sheath 90 has a non-circular cross-section 122. More preferably, the sheath 90 has an oblong cross-section 120, includes one or more tangent segments 144, oblique segments 184, or both. The oblong cross-section 120 may have a length that is greater than the width, have two circular portions that include separate centers, or both. The length may be a factor larger than the width. The length may be a factor greater than the width of about 1.2w or more, about 1.5w or more, about 1.75w or more, or even about 2w or more (where "w" is width). The oblong cross-section 120 may be generally oval, include one or more linear segments, or both. The oblong cross-section 120 may include one non-circular portion that includes at least two circular segments and one or more linear segments. The oblong cross-section 120 may have a perimeter that spans 360 degrees. The oblong cross-section 120 may have a portion with an inner diameter that is substantially the same as the outer diameter of the endoscope 60 and a portion with an inner diameter that is smaller than the outer diameter of the endoscope. The sheath 90 may function as an endoscope 60 cleaner. The sheath 90 may have a distal end 92 and a proximal end 94 with a longitudinal axis that extends therebetween.

The distal end 92 of the sheath 90 may function to direct irrigation fluid, suction, or both across the viewing lens, the distal end 62, or both of the endoscope 60. The distal end 92 may function to open, be open, or both so that irrigation fluid may exit the sheath 90. The distal end 92 may function to not interfere with the imaging capabilities of the endoscope 60. The distal end 92 may open out so that pressure of the irrigation fluid drops as the irrigation fluid reaches the distal end 92. The distal end 92 may be free of any integrally formed pieces that direct irrigation fluid, suction, or both across a distal end of the endoscope 60. The distal end 92 may be free of any extensions that extend from the distal end 92. The distal end 92 may be free of any pieces that extend from a portion of a distal most end of the sheath 90. The distal end 92 may be substantially equal around a circumference of the sheath 90. The distal end 92 may include one or more positioning features (e.g., dimples 134 or pins 224). The endoscope 60 may be eccentrically located within the distal end 92. The distal end 92 region may include one or more annular gaps 222 (e.g., a ring shaped gap).

The sheath 90 may include one or more lips. The one or more lips may be a flow director. The one or more lips may function to assist in directing irrigation fluid across the lens, imaging device, or both of the endoscope 60. The one or more lips may function to substantially mirror the shape of the endoscope 60. The one or more lips may overhang the endoscope 90. The one or more lips may provide a protective cover for the endoscope 90. The one or more lips may only be used when a flexible flap is used. The one or more lips may function as a distal end stop 228. The sheath 90 may be free of lips. The one or more lips may be located on a distal end 92 opposite a proximal end 94 of the sheath 90.

The proximal end 94 of the sheath 90 may function to create a connection with the endoscope 60. The proximal end 94 may align the sheath 90 relative to the endoscope 60. The proximal end 94 of the sheath 90 may axially align the sheath 90 relative to the endoscope 60, radially align the sheath 90 relative to the endoscope 60, axially align the distal ends 92, 62 of the sheath 90 and the endoscope 60, the sheath 90 axially relative to a light post 72 of the endoscope 60, the sheath 90 rotationally relative to a light post 72 of the endoscope 60, or a combination thereof. The proximal end 94 may receive all or a portion of the endoscope 60. The proximal end 94 may contact a shoulder 70 of the endoscope 60. A longitudinal axis may extend between the proximal end 94 and the distal end 92 of the sheath 90. The longitudinal axis may extend through a through hole 152, channel, lumen, or a combination thereof that extends the length of the sheath 90. The endoscope 60 may extend within the sheath 90 along the longitudinal axis. The longitudinal axis may extend from a connection point between the endoscope 60 and the sheath 90 and through a tube 96 of the sheath 90.

The tube 96 may function to receive the imaging device of the endoscope 60. The tube 96 may be located at the distal end 62 of the endoscope 60. The tube 96 may be generally the same size and shape as the endoscope 60. For example, if the endoscope 60 has a generally circular cross-section then the tube may have a generally circular cross-section 142. The tube 96 may have a shape that is different than the endoscope 60. The tube 96 may be any shape so that the tube 96 is configured to receive the endoscope 60. The tube 96 may be connected to: a hub 98, integrally formed with a hub 98, in fluid communication with a port 106, connected to a port 106, include a through hole 152 that is in communication with a port 106, or a combination thereof. The tube 96 may be connected to a handpiece at the proximal end 94. The tube 96 has a longitudinal axis and the shape of the tube 96 may be consistent along its length. The shape of the tube 96 may vary along the length of the tube 96. The tube 96 may be integrally formed with a handpiece. The tube 96 may have a uniform wall thickness, a variable wall thickness, or both. The wall thickness may vary along the length of the tube 96. The wall thickness may vary along the circumference of the tube 96. For example, the tube 96 may have a wall that is twice as thick on a bottom half of the tube as a top half of a tube when viewing the tube in a cross-section. The tube 96 may include one or more positioning devices 220 along its length and/or circumference. The one or more positioning devices 220 may be one or more dimples 134, one or more pins 224, one or more crimps 226, one or more end stops 228, or a combination thereof.

The one or more positioning devices 220 may function to position an endoscope 60 within a sheath 90. The one or more positioning devices 220 may function to axially align, radially align, longitudinally align, laterally align, or a combination thereof the endoscope 60 within a sheath 90. The one or more positioning devices 220 may extend along a portion of the length or the full length of the sheath 90, the tube 96 of the sheath 90, or both (e.g., a surface of the tube). The one or more positioning devices 220 may be located continuously between the distal end 92 and proximal end 94 of the sheath 90, periodically be located between the distal end 92 and the proximal end 94 of the sheath 90, or a combination of both. The one or more positioning devices 220 may be spaced apart. The one or more positioning devices 220 may be circumferentially spaced apart, longitudinally spaced part, laterally spaced apart, coplanar, non-coplanar, or a combination thereof. The one or more positioning devices 220 may be in a line such that each of the positioning devices 220 are coplanar and perpendicular to the longitudinal axis. The one or more positioning devices 220 may be staggered and coplanar (e.g., circumferentially spaced apart and longitudinally spaced apart). The one or more positioning devices 220 may be staggered and non-coplanar. The positioning devices 220 may only be located in the distal end 92 region, proximate to the distal end 92 region, on the distal end 92 side of the sheath 90, or a combination thereof. The positioning devices 220 may be positioned in groups and/or sets.

One group of positioning devices 220 may maintain the endoscope 60 a distance from the end of the sheath 90. The distance may be a sufficient distance so that the irrigation fluids are moved across the lens, imaging device, or both by surface tension. The distance between the distal end 92 of the sheath 90 and the distal end 62 of the endoscope 60 may be a distance so that surface tension moves an irrigation fluid across the lens, the imaging device, or both. For example, surface tension may cause the irrigation fluid to wrap around the imaging device, lens, or both of the endoscope 60 so that the endoscope 60 is cleaned. The distance between the distal end 62 of the endoscope 60 and the distal end 92 of the sheath 90 may be about 1 mm or more, about 2 mm or more, or about 3 mm or more. The distance between the distal end 62 of the endoscope 60 and the distal end 92 of the sheath 90 may be about 15 mm or less, about 12 mm or less, or about 10 mm or less. The surface tension may maintain fluid in contact with the lens, the imaging device, or both so that the lens, the imaging device, or both are washed, cleaned, or both. The one or more positioning devices 220 may both axially align the endoscope 60 and position the endoscope 60 within the sheath 90, the tube 96, or both.

The one or more positioning devices 220 may align the endoscope 60 within the tube 96, the sheath 90, or both. The one or more and preferably a plurality of positioning devices 220 may create an annular gap 222 around an endoscope 60. The annular gap 222 may be uniform around the endoscope 60. The annular gap 222 may vary in distance between the outer wall of the endoscope 60 and the inner wall of the sheath 90. The one or more and preferably a plurality of positioning devices 220 may move the endoscope 60 into contact with a wall of a sheath 90, a tube 96, or both so that a gap 222 is only created around a portion of the endoscope 60, a fluid is prevented from extending between a contact location between the endoscope 60 and sheath 90, or both. An offset gap 222 may be created so that a center of the sheath 90 and a center of the endoscope 60 are offset, eccentric, shifted relative to each other, or a combination thereof. For example, the endoscope 60 may be shifted all the way to one wall so that a gap 222 is only located on one side of the endoscope 60. The one or more positioning devices 220 may function to be an axial stop. The one or more positioning devices 220 may move the endoscope 60 into contact with a surface (e.g., the tube 96, the sheath 90, or both) so that a fluid barrier is created.

The fluid barrier may function to prevent fluid from flowing between the endoscope 60 and the sheath 90, the tube 96, a surface of the sheath and/or tube, or a combination thereof. The fluid barrier may prevent fluid from passing around a portion of the endoscope 60 (e.g., an arc length of 15 degrees or more, 30 degrees or more, 45 degrees or more, 60 degrees or more, 105 degrees or more, 135 degrees or more, or even about 180 degrees or less). The fluid barrier may be a seal that prevents fluid from passing axially around a portion of the endoscope 60. The fluid barrier may prevent passage of irrigation fluid, suction, or both between a distal end 92 and a proximal end 94 of the surface, the tube 96, the sheath 90, or a combination thereof. The fluid barrier may be located adjacent to a channel, a conduit, a lumen, or a combination thereof. The fluid barrier may only be created when the endoscope 60 is eccentrically located within the tube 96 of the sheath 90. The positioning devices 220 may move the endoscope 60 so that an arc length of the endoscope 60 is in contact with the tube 96 of the sheath 90 (e.g., barrier portion). The arc length of the endoscope 60 in contact with the tube 96 of the sheath 90 may be about 30 degrees or more, about 45 degrees or more, about 60 degrees or more, about 75 degrees or more, about 90 degrees or more, or even about 105 degrees or more. The arc length of the endoscope 60 in contact with the tube 96 of the sheath 90 may be about 180 degrees or less, about 165 degrees or less, or about 135 degrees or less. The arc length may form a cradle that wraps around and retains an endoscope 60 within a portion of the tube 96 and/or sheath 90. The cradle may be a circular portion and/or circular segment 142. The cradle may be connected to an opposing cradle by two straight segments (i.e., tangent segments 146, oblique segments 184, or both). The cradle may be part of an obround tube. The cradle may have an arc length as is discussed herein. The cradle may extend from about 30 degrees to about 180 degrees and preferably from about 60 degrees to about 180 degrees. The one or more positioning devices 220 may be a unitary part, a non-unitary part, or both that positions the endoscope 60 within the tube 96 of the sheath 90.

The positioning devices 220 may be an integral part, a unitary part, a non-unitary part, or a combination thereof of the sheath 90. The positioning devices 220 may be added to the sheath 90, the tube 96, or both (i.e., non-unitary). The positioning devices 220 may be a non-welded piece, non-soldered piece, or both that is added to the sheath 90, the tube 96, or both. The positioning devices 220 may be an added piece of material that is connected to the sheath 90, the tube 96, or both. The positioning devices 220 may be added without heating the positioning devices 220, the tube 96, the sheath 90, or a combination thereof (i.e., liquefying material or adding molten material). The positioning devices 220 may be connected to the sheath 90, the tube 96 of the sheath 90, or both by one or more fasteners. The positioning devices 220 may be connected to the tube 96, the sheath 90, or both by an adhesive, a threaded connection, a rivet like connection, a friction fit, a mating member that extends through the tube 96 and/or sheath 90, or a combination thereof. The positioning devices 220 may form a connection so that the positioning features 220 extend out from an inside wall of the tube 96 and/or sheath 90 and form a substantially flush connection with an outside wall of the tube 96.

The one or more positioning devices 220 may be a formed part of the sheath 90, the tube 96, or both such that no additional material is added (i.e., unitary). The one or more positioning devices 220 may be a portion that is dented, formed, crushed, pressed, molded, or a combination thereof. The one or more positioning devices 220 may be created by cutting a portion of the sheath 90, the tube 96, or both and repositioning the piece of cut material (e.g., a crimp 226). The sheath 90 may be formed so that the sheath 90 includes one or more positioning devices 220. The sheath 90 may include a plurality of positioning devices 226. The positioning devices 220 may be located on an inner wall, an outer wall, be part of the wall, extend through the wall, or a combination thereof of the sheath 90 and/or tube 96.

The sheath 90 may include one more sets and/or groups of positioning devices 220. Preferably, the sheath 90 includes two or more sets and/or groups of positioning devices 220. More preferably, each of the two or more sets and/or groups of positioning devices 220 include two or more positioning devices 220. For example, one set of two or more positioning devices 220 may be located in the distal end 92 region (i.e., last 10 percent of the sheath 90) and another set of two or more positioning devices 220 may be located between the distal end 92 region and the proximal end 94. When more than one positioning device 220 is present the positioning devices 220 may be located at angle relative to each other. The two or more positioning devices 220 may be equally spaced apart. For example, if there are two positioning devices 220 the devices may be 180 degrees apart and there are three positioning devices 220 the positioning devices may be 120 degrees apart. The two or more positioning devices 220 may be spaced apart about 15 degrees or more, about 30 degrees, or more, about 45 degrees or more, about 60 degrees or more, about 90 degrees or more, about 120 degrees or more, or even about 150 degrees or more apart. The two or more positioning devices 220 may be located about 180 degrees or less or about 160 degrees or less apart.

Each sheath 90 may include one or more groups/sets, two or more groups/sets, three or more groups/sets, or even four or more groups/sets of positioning devices 220. Each group of sets may include one or more, two or more, three or more, or even four or more positioning devices 220. Each of the groups/sets of positioning devices 220 may be aligned along an axis, offset along an axis, rotationally offset, rotationally aligned, coplanar, non-coplanar, or a combination thereof relative to another group/set of positioning devices 220. Preferably, each group/set of positioning devices 220 may be substantially the same distance from the distal end 92, the proximal end 94, or both. Each of the groups/sets of positioning devices 220 may be aligned along an axis, offset along an axis, rotationally offset, rotationally aligned or a combination thereof within a group. The positioning devices 220 may be a circular portion, a circular segment, a dimple 134, a pin 224, a crimp 226, an end stop 228, a tangent portion 144, a tangent segment 146 (or line), an oblique portion 182, an oblique segment 184 (or line), or a combination thereof and the teachings as to the positioning devices 220 are incorporated by reference herein for each of the various types of positioning devices.

The one or more dimples 134 may function to position an endoscope 60 within a sheath 90, a tube 96 of the sheath 90, or both. The one or more dimples 134 may function to axially position the endoscope 60 within the sheath 90 (e.g., form an axial stop). The one or more dimples 134 may function as a distal end 92 stop, a locator, an axial locator, a cross-sectional locator (e.g., shift the sheath 90 within the cross-section of the sheath 90), or a combination thereof. For example, the one or more dimples 134 may be used to create an annular gap 222, an offset gap 222, or both. The one or more dimples 134 may contact a point of the endoscope 60 along the length of the endoscope 60. The one or more dimples 134 may function to position the endoscope 60 within the sheath 90 so that a conduit, channel, lumen, space, or a combination thereof is created along all or a portion of the longitudinal axis of the endoscope 60, sheath 90, or both. The one or more dimples 134 may create a space, a conduit, a lumen, a channel, or a combination thereof between a wall of the sheath 90 and the endoscope 60. The one or more dimples 134 may be a portion of the wall of the sheath 90 that extends inward (e.g., towards a center of the sheath 90). The one or more dimples 134 may be generally round, square, oval, triangular, rounded, have a flat surface, have a rounded surface, be hemispherical, or a combination thereof.

The one or more dimples 134 may be an indentation and/or deformation in the side of the sheath 90, the tube 96, or both without adding material, without removing material, without relocating material, or a combination thereof. The one or more dimples 134 may be located on opposing sides of the tube 96. The one or more dimples 134 may be radially spaced apart, axially spaced apart, longitudinally spaced apart, or a combination thereof. The one or more dimples 134 may be located along the length. For example, the tube 96 may include dimples 134 that are spaced apart from the proximal end 94 to the distal end 92 so that the endoscope 60 and sheath 90 are fully supported relative to each other along their respective lengths. If more than one dimple 134 is present the dimples 134 may be located adjacent, in the same plane, in a line, be axially spaced apart, radially spaced apart, coplanar, non-coplanar, or a combination thereof. When more than one dimple 134 is present the dimples 134 may be in a straight line relative to the longitudinal axis, perpendicular to the longitudinal axis, at an angle relative to the longitudinal axis, or a combination thereof. When more than one dimple 134 is present the dimples 134 may be separated by an angle of about 180 degrees or less, about 150 degrees or less, about 120 degrees or less, about 90 degrees or less, or even about 60 degrees or less. The two or more dimples 134 may be separated by an angle of about 15 degrees or more, about 30 degrees or more, or even about 45 degrees or more. The sheath 90 may include about 2 or more dimples 134, 3 or more dimples 134, 4 or more dimples 134, 5 or more dimples 134, or even about 6 or more dimples 134. Two or more dimples 134 may be located generally within the same plane and radially spaced apart so that the dimples offset the endoscope 60 within the sheath 90 (e.g., the center of the endoscope 60 and the center of the sheath 90 are not in line). The one or more dimples 134 may be located on the same side of the sheath 90 as the port 106, opposite side of the sheath 90 as the port 106, at an angle relative to the port, or a combination thereof. The one or more dimples 134 may be used in conjunction with one or more tangent segments 146, one or more oblique segments 184, one or more pins 224, one or more crimps 226, one or more end stops 228, or a combination thereof.

The one or more pins 224 may function to bolster the distal end 92 of the sheath 90, the tube 96, or both. The one or more pins 224 may function to provide an axial end stop 228. The one or more pins 224 may function to provide axial stability to the endoscope 60 so that that endoscope 60 cannot be forced in an axial direction. The one or more pins 224 may be a non-unitary part, a non-integral part, or both that is added to the sheath 90, the tube 96, or both. The one or more pins 224 may be connected to the tube 96, the sheath 90, or both using one or more of the fasteners discussed herein. The one or more pins 224 may be connected to the sheath 90, the tube 96, or both without a welded connection. The one or more pins 224 may connect to the tube 96, the sheath 90, or both so that so that the pins 224 are flush with an outer surface of the tube 96, the sheath 90, or both. When more than one pin is present the pins 224 may be the same size and/or different sizes. The cross-sectional length of the pins may be varied. For example, the base may be larger than the tip. The one or more pins 224 may provide a higher axial stiffness when compared to a dimple 134. The one or more pins 224 may be smaller than a dimple 134. The one or more pins 224 may be longer than a dimple 134 (i.e., extend further towards a center of the tube 96 and/or sheath 90 than a dimple 134). The one or more pins 224 may be located at an end of the distal end 92. For example, the pins 224 may be located closer to the end when compared to a dimple 134. The one or more pins 224 may have a portion that provides axial alignment and a portion that includes radial alignment.

The one or more pins 224, one or more crimps 226, one or more end stops 228, or a combination thereof may function to prevent axial movement of an endoscope 60 within the sheath 90, a tube 96 of the sheath 90, or both. Preferably, the one or more pins 224, one or more crimps 226, one or more end stops 228, or a combination thereof may prevent axial movement towards the distal end 92. The one or more pins 224, one or more crimps 226, one or more end stops 228, or a combination thereof may function to create a gap 222 between the sheath 90 and the endoscope 60. The one or more pins 224, one or more crimps 226, one or more end stops 228, or a combination thereof may offset the endoscope 60 within the sheath 90 so that the gap 222 is located around a portion of the endoscope 60 (i.e., the gap is not an annular gap). The one or more pins 224, one or more end stops 228, or both may be added to the sheath 90 and the pins 226 may extend towards a center of the endoscope 60.

The one or more crimps 226 may be material that is cut and folded. The one or more crimps 226 may function to be an axial end stop. The one or more crimps 226 may function to position an endoscope 60 within the sheath 90, the tube 96, or both. The one or more crimps 226 may be bent from a terminal end inwards and extend in the direction of the longitudinal axis. The one or more crimps 226 may extend from the terminal end and may be angled towards a center of the sheath 90, the tube 96, or both. For example, an end of the crimp 226 may be folded sideways inwards so that the crimp points towards an opposing wall and/or opposing crimp 226. The one or more crimps 226 may be added material that is shaped to create an axial stop, to locate the endoscope 60 within the sheath 90, or both. The one or more end stops 228 may be material that is welded, adhered, soldered, brazed, or a combination thereof to the end of the sheath 90, or a combination thereof. When more than one pin 224, one or more crimps 226, one or more end stops 228, or a combination thereof is present the length may be varied, the same, or both. The pins 224, one or more crimps 226, one or more end stops 228, or a combination thereof may maintain the endoscope 60 a distance from the distal edge of the endoscope sheath 90. The one or more pins 224 may be used in conjunction with one or more dimples 134, one or more crimps 226, or both.

The one or more tangent segments 146 may function to decrease the size, diameter, arc length, or a combination thereof of the sheath 90 at one or more locations. The one or more tangent segments 146 may function to create a cross-sectional area of the sheath 90 that is smaller than the endoscope 60, a cross-sectional area greater than the endoscope 60, or both so that the endoscope 60 is positioned at an offset within the sheath 90. The one or more tangent segments 146 may function to create a space, a lumen, a channel, an opening, a gap, or a combination thereof so that a functional device, irrigation fluid, suction, debris, or a combination thereof may pass through the sheath 90. The one or more tangent portions 144, tangent segments 146, or both may create a sheath 90 with a cross-sectional shape that is non-circular, oblong, egg shaped, oval, ellipse, obround, or a combination thereof. The one or more tangent segments 146 may include a point of contact 223 with the endoscope 60 when viewed in the cross-section. The one or more tangent segments 146 may be generally planar. The one or more tangent portions 146 may be a line and/or segment when viewed in the cross-section. The one or more tangent segments 146 may extend at an angle relative to the perimeter (i.e., outside) of the endoscope 60 when viewed in the cross-section. When more than one tangent lines are used the tangent lines may diverge on one end and converge on the other end. When two or more tangent lines are used any angle is formed between the tangent lines so that a channel, lumen, space, opening, conduit, gap, or a combination thereof are formed. The angle of the tangent portion 144 may be about 15 degrees or more, about 30 degrees or more, about 45 degrees or more, or about 60 degrees or more relative to a plane that bisects the sheath 90. The angle of the tangent portion 144 may be about 160 degrees or less, about 125 degrees or less, or even about 105 degrees or less relative to a plane that bisects the sheath 90. For example, the tangent segments 146 extend at an angle relative to a plane that bisects the sheath 90 along its longitude when viewed in the cross-section. The one or more tangent segments 146 may be a tangent line or tangent plane that extends along all or a portion of the sheath 90.

The tangent portion 144 may function to run the length of the sheath 90 and form a tangent segment 146 when viewed in the cross-section. The tangent portion 144 may be a plane that extend along all or a portion of the length of the sheath 90. The tangent portion 144 may include a top portion and a bottom portion where an angle and/or shape of the tube 96 changes. The tangent portion 144 may include a change in shape between the tangent portion 144 and the circular portion 142, between the circular segment 145 and the tangent segment 146, or both. For example, a crease may be formed in the sheath 90 and the crease may be one or more edges of the tangent portion 144. The tangent portion may have a pair of opposing edges that are generally parallel and a part of the sheath 90 between the edges forms a line of contact 223 with the endoscope 60 so that the endoscope is shifted, positioned, moved, aligned, or a combination thereof within the sheath 90.

The tangent portion 144 may include one or more tangent segments 146. The tangent portions 144 are a part of the tube 96 of the sheath 90 when the sheath 90 is viewed and discussed herein in three dimensions and the tangent segments 146 and/or tangent lines are a part of the tube 96 of the sheath 90 when viewed and discussed herein as two dimensional (i.e., viewed in the cross-section). The tangent portion 144 may include one or more tangent segments 148 that align an endoscope 60 with a sheath 90. The tangent portion 144 may function to align an endoscope 60 within a sheath 90. The tangent portion 144 may function to locate an endoscope 60 along a top, bottom, left, or right side of the sheath 90. The tangent portion 144 may locate the endoscope 60 so that a center of the endoscope 60 and the center of the sheath 90 are offset. The tangent portion 144 may be shaped so that the sheath 90 has an oblong shape 120, is non-circular, one or more flat walls, one or more linear walls, one or more walls with a single point 223 (or line) of contact with an endoscope 60, or a combination thereof. The tangent portion 144 may assist in forming a lumen, a channel, a conduit, or a combination thereof within the sheath 90, between the sheath 90 and the endoscope 60, or both. The tangent portion 144 may have two or more tangent segments 144 that extend at an angle relative to each other. The tangent segments 144 may include one or more circular segments 145, one or more tangent segments 146, or both.

The one or more tangent segments 146 may function to extend between a first end and a second end so that a conduit, lumen, channel, a gap, or a combination thereof is created within the sheath 90. The one or more tangent segments 146 as discussed herein, unless otherwise stated, are discussed in a cross-section, but are part of a larger portion that extends partially or fully along a length of the sheath 90. The one or more tangent segments 146 may function to align the endoscope 60 within the sheath 90. The one or more tangent segments 146 may contact the endoscope 60 at a point so that the endoscope 60 is shifted within the sheath 90. Preferably, the sheath 90 includes two tangent segments 146 that angle towards each other on one end and diverge away from each other on a second end. The one or more tangent segments 146 may be generally planar, linear, or both. The one or more tangent segments 146 may be concave, convex, include a concave portion, a convex portion, or a combination thereof. The one or more tangent segments 146 may directly connect. For example, the sheath 90 may not include a circular segment and the tangent segments 146 may connection together forming a tube 96 with a conduit, lumen, channel, gap, or a combination thereof. The tangent segments 146 may be free of a connection with a circular segment 145. The one or more tangent segments 146 may connect two opposing circular segments 145. The one or more tangent segments 146 may have a tangent point with each of the one or more circular segments 145. The one or more tangent segments 146 may have a tangent point 223 with both the endoscope 60 and the circular segments 145. The one or more tangent segments 146 may extend between a circular portion 142 and a circular segment 145.

The one or more circular segments 145 may be connected to a tangent segment 146 on one or both sides, a oblique segment 184 on one or both sides, or both. The circular segments 145 as discussed herein, unless otherwise stated, are discussed in the cross-section, but are a part of a larger portion that extends partially or fully along a length of the sheath 90. The circular segment 145 may have a radius that is substantially the same as the radius of the endoscope 60 (i.e., slightly larger so that the endoscope 60 fits within the sheath 90). The circular segment 145 may have a radius that is greater than the radius of the endoscope 60. Preferably, at least one circular segment 145 has a radius that is less than the radius of the endoscope 60 so that the tangent segments 146 diverge and contact the endoscope 60 and a channel, a lumen, a conduit, gap, or a combination thereof is formed between the circular segment 145 and the endoscope 60. More preferably, at least one of the circular segments 145 has a radius that is greater than the radius of the endoscope 60 and at least one of the circular segments 145 has a radius that is less than the radius of the endoscope 60. The one or more circular segments 145 may have a center that aligns with a center of the endoscope 60. Preferably, the center of the endoscope 60 and the center of the circular segments 145 are offset so that the endoscope 60 is shifted to one side and/or end of the tube 96. The one or more circular segments 145 may be a continuous arc, have a plurality of linear portions that are connected together in an arcuate pattern, or both. The one or more circular segments 145 may function to connect to two segments that generally face in the same direction. The one or more circular segments 145 may have two ends that generally point in the same direction. The one or more circular segments 145 may have a first end and a second end that are about 180 degrees or more from each other. The first end and the second end may be located about 90 degrees or more apart, preferably about 105 degrees or more apart, more preferably about 125 degrees or more apart, even more preferably about 160 degrees or more apart, and most preferably about 175 degrees or more apart. The one or more circular segments 145 may form an end piece. The one or more circular segments 145 may include two 90 degree portions. For example, the circular segment 145 may be generally square in shape or include a square shaped portion and circle around so that both ends face the same direction. The circular segment 145 may be triangular in shape or include a triangular shaped portion. The circular segments 145 may be tangent to one or more tangent segments 146, one or more oblique segments 184, or both. The circular segments 145 may be part of the tangent portion 144, the circular portion 142, or preferably both.

The one or more circular portions 142 may include one or more circular segments 145. The one or more circular portions 142 may function to receive all or a portion of an endoscope 60. The one or more circular portions 142 may be located opposite the tangent portion 144, connected to the tangent portion 144, or both. The one or more circular portions 142 may be the larger side and/or end of the sheath 90 when compared to the tangent portion 144. The one or more circular portions 142 may be any portion with a radius, an arc length, or both. The one or more circular portions 142 may include one or more circular segments 145 as discussed herein. The one or more circular portions 142 may generally mirror the shape of the endoscope 60. The one or more circular portions 142 may terminate at the tangent portions 144, at the tangent segments 146, oblique segments 184, oblique portions 182, or a combination thereof. The circular portion 142 may have a length that is substantially equal to the length of the tangent portion 144. For example, the perimeter of the cross-section of the sheath 90 may be equally divided between the circular portion 142 and the tangent portion 144. The one or more circular portions 142 may be connected to one or more oblique segments 184, one or more tangent segments 146, or both. The one or more oblique segments 184 may be part of an oblique portion 182 that may extend all or a portion of a length of the sheath 90.

An oblique portion 182 may extend from a first end towards a second end of the tube 96 and/or sheath 90. The one or more oblique portions 182 may terminate before the oblique portions reach a second end of the tube 96 and/or sheath 90. The one or more oblique portions 182 may function to create a planar portion (i.e., a oblique segment 184) along a perimeter of the sheath 90 when the sheath is viewed in the cross section. As discussed herein oblique portion 182 is three dimensional and oblique segment 184 and/or line is two dimensional (i.e., a cross-section). The one or more oblique portions 182 may function to laterally displace, radially displace, circumferentially displace, or a combination thereof the endoscope 60 within the sheath 90. Preferably, the oblique portions 182 do not extend from one end to the second end e.g., a distal end 92 to a proximal end 94). More preferably, the oblique portions 182 extend to one end of the sheath 90 only. The oblique portions 182 may terminate before the oblique portions 182 reach one or both ends. The oblique portions 182 may at least partially helically rotate as the oblique lines longitudinally extend along the length of the sheath 90. The oblique portions 182 may partially or fully rotate about the sheath 90, partially or fully helically wrap the sheath 90, or both. The oblique portions 182 may wrap about 5 degrees or more, about 10 degrees or more, about 15 degrees or more around the sheath 90. The oblique portions 182 may wrap about 180 degrees or less, about 135 degrees or less, about 105 degrees or less, about 90 degrees or less, or even about 60 degrees or less of the sheath 90. If more than one oblique portion 182 is present, one oblique portion may be straight and one oblique portion may extend at an angle. The one or more oblique portions 182 may include two edges and one edge may extend parallel straight between the distal end 92 and the proximal end 94 and the second edge may extend at an angle relative to the first edge as the second edge extends from the distal end 92 towards the proximal end 94. The oblique portions 182 may be located at the distal end 92 only, in a distal end 92 region, or both. The one or more oblique portions 182 may be located on opposing sides of the sheath 90. All or a portion of the oblique portion 182 may be tangent to an endoscope 60, a circular portion 142 of the tube 96, or both when viewed in the cross-section. The oblique portion 182 when viewed in the cross section may have one or more tangent segments 146, tangent lines, or both. Two or more oblique portions 182 may be located on each side so that two or more oblique segments 184 are formed.

The oblique segments 184 may function to create a part of the sheath 90 that contacts the endoscope 60 so that the endoscope 60 is shifted to one side of the sheath 90. The oblique segments 184 as discussed herein, unless otherwise stated, are discussed in the cross-section, but are a part of a larger line that extends partially or fully along a length of the sheath 90. The oblique segments 184 may function to create a channel, a lumen, a conduit, a gap, or a combination thereof at one end of a sheath 90 and be substantially free of a defined channel, lumen, conduit, a gap, or a combination thereof at a second end (i.e., formed from a non-circular portion). The oblique segments 184 may function to shape the sheath 90 so that the sheath 90 has a non-circular shape, is oblong, oval, elliptical, egg shaped, obround, or a combination thereof. The oblique segments 184 may gradually shorten in length so that as cross-sections are taken from the distal end 92 towards the proximal end 94. The oblique segments 184 may terminate before the proximal end 94 so that a cross-section taken proximate to the proximal end 94 will be free of oblique segments 184. The oblique segments 184 may be generally planar, linear, straight, flat, be concave, be convex, or a combination thereof. The oblique segments 184 may be tangent to the circular portions 142, the circular segments 145, the endoscope 60, or a combination thereof. The oblique segments 184 may connect two circular segments 145 together. The oblique segments 184 may result in one end of the sheath 90 being circular and one end of the sheath 90 being non-circular (e.g., oblong).

A perimeter of the circular end and the non-circular end may be equal. A perimeter of the distal end 92 and the proximal end 94 may be equal. A cross-sectional length of the largest portion of the non-circular end may be the same as or greater than the cross sectional length of the largest portion of the circular end. The cross-sectional area of the circular end may be the same as the cross-sectional area of the non-circular end. The cross-sectional area of the distal end 92 may be the same as the cross-sectional area of the proximal end 94. The area of the non-circular end may be greater than the area of the circular cross-sectional end. The area of the non-circular end may be sufficiently large so that a conduit, channel, lumen, or a combination thereof is created that may transfer irrigation fluid, suction, a functional device, or a combination thereof. The area of the non-circular end may function to transport items moved into the sheath 90 through the port 106.

The port 106 may function to provide access into the tube 96 of the sheath 90. The port 106 may function to provide a fluid connection, a connection with one or more irrigation sources 4, a connection with one or more suction sources 10, one or more common lines 18, one or more delivery lines 42, or a combination thereof. The port 106 may form a fixed connection with one or more lines so that suction, irrigation fluid, or both may be provided through the port 106. The port 106 may provide direct access to the inside of the tube 96. The port 106 may be configured so that one or more functional elements (e.g., a cutting tool, a cauterizing tool, or both) may gain access to the inside of the tube 96 of the sheath 90, may extend out of the distal end 92 of the sheath 90, or both. For example, the port 90 may not be receive items that flow. The port 106 may be part of a handpiece of the sheath 90. The port 106 may be part of the tube 96, the hub 98, or both.

The hub 98 may function to connect the sheath 90 to the endoscope 60. The hub 98 may function to seal the sheath 90 to the endoscope 60. The hub 98 may surround a portion of the endoscope 60. The hub 98 may function to create a fluid seal with the endoscope 60 so that irrigation fluid, suction, or both do not leak. The hub 98 may receive a shoulder 70 of the endoscope 60 so that the shoulder 70 and the hub 98 form a fluidly sealed connection. The hub 98 may have a circular cross section. The hub 98 may taper as it extends towards the distal end 92 of the sheath 90. The hub 98 may be large enough to receive all or a portion of the endoscope 60. The hub 98 may partially extend around the endoscope 60, fully extend around the endoscope 60, or a combination of both. The hub 98 may have a thicker section that connects to the tube 96. The hub 98 may be fastened to the tube 96. The hub 98 may be connected to the tube 96 by a mechanical fastener such as threads, a snap, a one way connection system, a series of ribs, or a combination thereof. The hub 98 may connect to the tube 96 by one or more adhesives. The hub 98 may include a collar 100, an arm, or both that receive all or a portion of the endoscope 60.

The collar 100 may be an integral part of the hub 98. The collar 100 may function to axially align, rotationally align, or both the endoscope 60 and the sheath 90. The collar 100 may form a majority of the hub 98 (e.g., 50 percent or more, 60 percent or more, or 70 percent or more). The collar 100 may function to prevent rotational movement. The collar 100 may function to prevent axial movement. The collar 100 may function to receive all or a portion of the endoscope 60. The collar 100 may function to receive a light post 72 of the endoscope 60. The collar 100 may surround the light post 72. The collar 100 may extend partially around the light post 72. The collar 100 and/or a region proximate to the collar may include one or more spacers 128.

The one or more spacers 128 may function to axially align the endoscope 60 within the sheath 90. The one or more spacers 128 may contact a shoulder 70 of the endoscope 60 and align the endoscope 60 within the sheath 90. The spacer 128 may contact an endoscope 60 so that the endoscope 60 is axially aligned within the tube 96. The one or more spacers 128 may be optional. The spacer 128 may be located proximate to one or more O-rings 130.

The one or more O-rings 130 may function to form a seal between the sheath 90 and a tube of the endoscope 60. The one or more O-rings 130 may function to prevent fluid from traveling towards the proximal end 64 of the endoscope 60. The one or more O-rings 130 may function to create a seal. The one or more O-rings 130 may be located within the hub 98, proximate to a collar 100 of the hub 98, or both. The one or more O-rings 130 may be made of any material that forms a seal. The one or more O-rings 130 may create a circumferential seal, a thrust seal, or both. The one or more O-rings 130 may be axially compressed, radially compressed, radially expanded, or a combination thereof. The one or more O-rings 130 may include one or more through holes 152. The one or more O-rings 130 may elastically deform. The one or more O-rings 130 may be made of an elastomer, include elastic, include rubber, include a deformable material, include a deformation region, or a combination thereof. The one or more O-rings 130 may be located proximate to a locking ring 132.

The one or more locking rings 132 may lock the O-ring 130 to the sheath 90, the endoscope 60, or both. The one or more locking rings 132 may function to lock two or more components together. The one or more locking rings 132 may include a through hole 152 so that the endoscope 60 extends through the tube 96 and the locking ring 132.

A through hole 152 may extend from a proximal end 94 to a distal end 92 of the sheath 90. A through hole 152 may be sufficiently large so that the endoscope 60 and fluid (e.g., irrigation fluid, suction, or both) may pass from the distal end 92 to the proximal end 94 of the sheath 90. The tube 96 may include one or more through holes 152 in the sheath 90. The through hole 152 in the tube 96 may open directly to a point of interest, an internal location of a patient, or both. The through hole 152 may include one or more flow directors.

FIG. 1A illustrates a top view of sheath 90 for use with an endoscope cleaner system (not shown). The sheath 90 includes a distal end 92 and a proximal end 94. A tube 96 and hub 98 extend between the distal end 92 and the proximal end 94. The hub 98 includes a port 106 for receiving suction, an irrigation fluid, or both. The hub 98 as shown has a collar 100 that includes an optional socket 102 for receiving a light post 72 (not shown) of a corresponding device (not shown) and the socket 102 includes an undercut 104 for forming a connection with the corresponding device.

FIG. 1B illustrates an end view of the sheath 90 from the proximal end 94. The port 106 is shown extending from the hub 98 and a through hole 152 is shown extending through the tube 96 and hub 98. The socket 102 is illustrated extending through the hub 98 towards the port 106. FIG. 1C illustrates a view of the sheath 90 from the distal end 92. A through hole 152 is shown extending through the sheath 90.

FIG. 2 illustrates a cross sectional view of the sheath 90 of FIG. 1A cut along lines A-A of FIG. 1C. The sheath 90 includes a tube 98 connected to a hub 98. The hub 98 includes a spacer 128 between an end of the tube 96 and a mating surface of the hub 98. An O-ring 130 is located in the hub proximate to a locking ring 132 for creating connection between the hub 98 and an endoscope (not shown). The tube 96 includes a dimple 134 along the longitudinal axis of the tube 90.

FIG. 3A illustrates an endoscope 60 extending into a sheath 90. The endoscope 60 includes a proximal end 64 including a visual port 74. The visual port 74 allows a user to view locations of interest located within the viewing cone 78 at the distal end 62 of the endoscope 60. The endoscope 60 includes a distal end 62 that extends to a distal end 92 of a sheath 90. The tube 96 of the sheath 90 includes a dimple 134 along its longitudinal axis that locates the endoscope 60 within the sheath 90. The sheath 90 includes a tube 96 extending from a distal end 92 to a hub 98. The hub 98 includes a port 106 for receiving suction, an irrigation fluid, or both. The hub 98 terminates at a proximal end 94 that receives a shoulder 70 and a light post 72 of the endoscope 60.

Figure 3B:
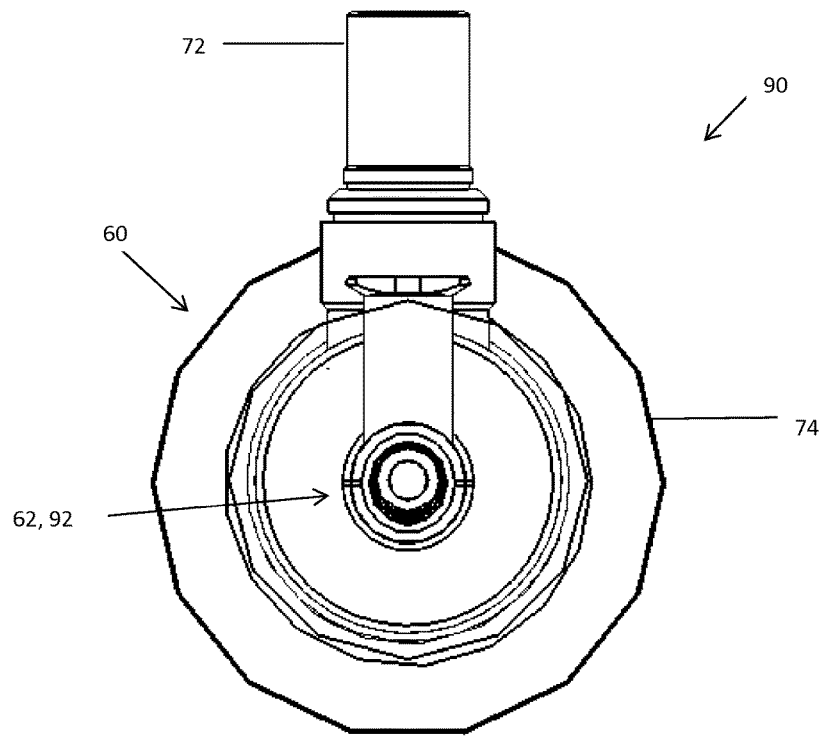
FIG. 3B illustrates a distal end view of FIG. 3A.

FIG. 3B illustrates an end view of the sheath 90 and endoscope 60 from a distal end 62, 92 respectively. The visual port 74 and light post 72 of the endoscope 60 extend outward from the endoscope 60.

Figure 4A:
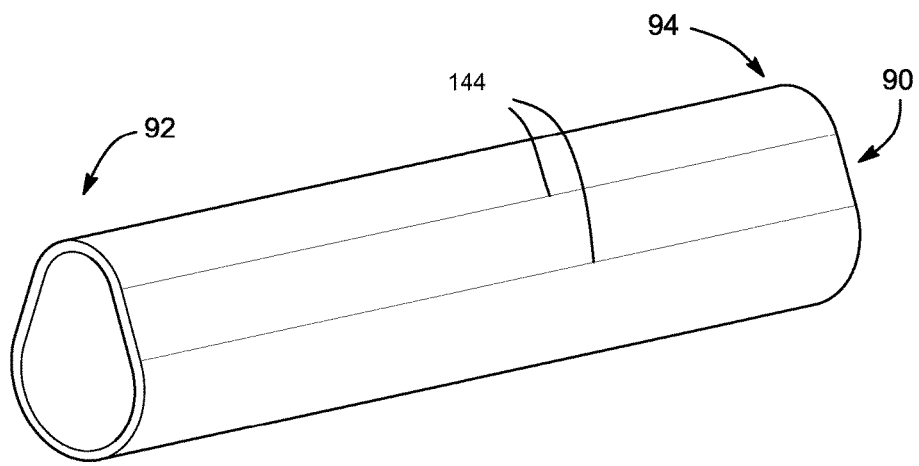
FIG. 4A illustrates a side view of a sheath having a non-circular perimeter.

FIG. 4A illustrates a perspective view of a sheath 90 including a tangent portion 144 that extend from the distal end 92 to the proximal end 94 so that a non-circular perimeter is formed along the longitudinal axis of the sheath 90.

Figure 4B:
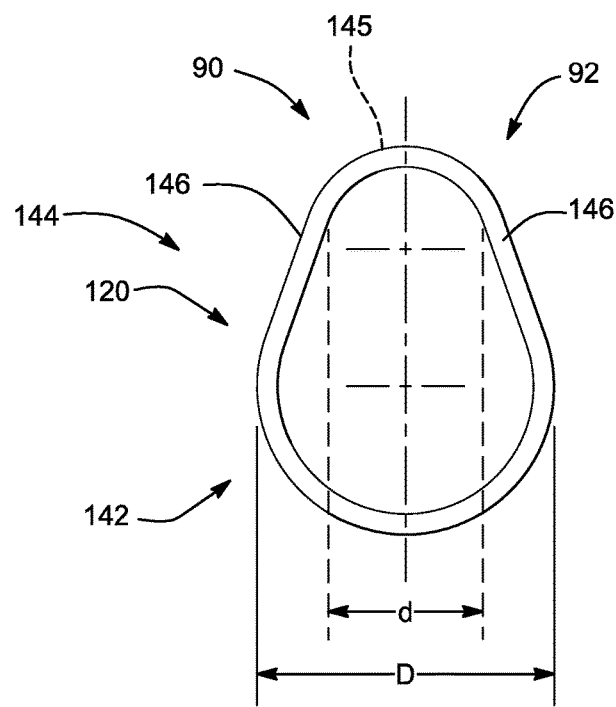
FIG. 4B illustrates a distal end view of the sheath of FIG. 0.4A.

FIG. 4B illustrates a distal end 92 view of the sheath 90. The distal end 92 of the sheath 90 has an oblong opening 120. The oblong opening 120 includes a circular portion 142 and a tangent portion 144. The tangent portion 144 includes two tangent segments 146 that are linear and a circular segment 145. The circular portion 142 and the tangent portion 144 are connected by the tangent segments 146. As illustrated, the circular portion 142 includes a diameter (D) and the tangent portion 144 includes a diameter (d) which is less than the diameter (D).

FIG. 5A illustrates a perspective view of a sheath 90 having oblique portions 182 that extend from the distal end 92 towards the proximal end 94 but the oblique portions 182 do not extend to the proximal end 94. The oblique portions 182 as illustrated partially helically wrap the sheath 90 as the oblique portions 182 extend from the distal end 92 to the proximal end 94 so that opposing edges of the oblique portions 182 converge and terminate.

FIG. 5B illustrates an end view of the sheath 90 from the distal end 92. The distal end 92 of the sheath 90 has an oblong shaped opening 120. The oblong opening 120 includes an oblique portion 182 having oblique segments 184 that are generally linear and connect the oblique portion 182 to a circular portion 142. The oblique portion 182 has oblique segments 184 that are also tangent segments 146, which are tangent to both the circular segment 145 of the circular portion 142 and the circular segment of the oblique portion 182.

FIG. 5C illustrates an end view of the sheath 90 from the proximal end 94. The proximal end is generally circular and is free of the oblique segments. The distal end 92 and the proximal end 94 (shown in FIGS. 5A and 5B) have a perimeter that are substantially equal.

Figure 6A:
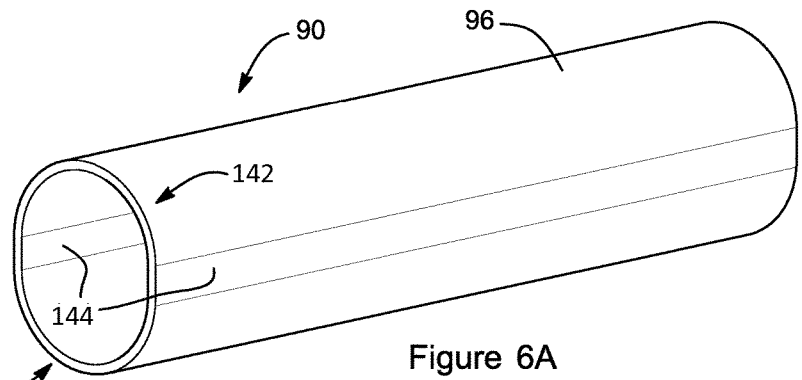
FIG. 6A illustrates a perspective view of a sheath having an oblong or obround shape.

FIG. 6A illustrates a perspective view of a tube 96 of the sheath 90. The tube 96 is oblong shaped 120 (i.e., obround) including two circular portions 142 that are connected by two tangent portions 144.

Figure 6B:
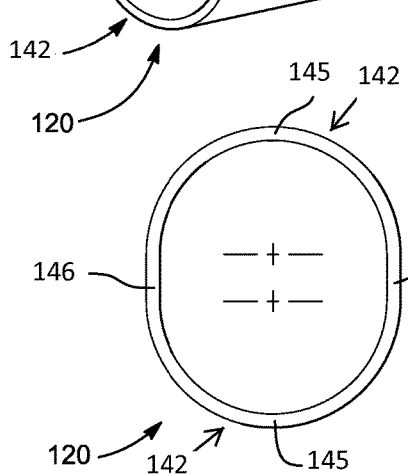
FIG. 6B illustrates an end view of the sheath of FIG. 6A.

FIG. 6B illustrates an end view of the sheath 90 of FIG. 6A. The sheath 90 has an oblong shape 120 (i.e., obround) with two opposing circular segments 145 that are connected together by tangent segments 146 when shown in the end view (i.e., a cross-sectional view). The two opposing circular segments 145 are cradles that form the obround shape.

Figure 6C:
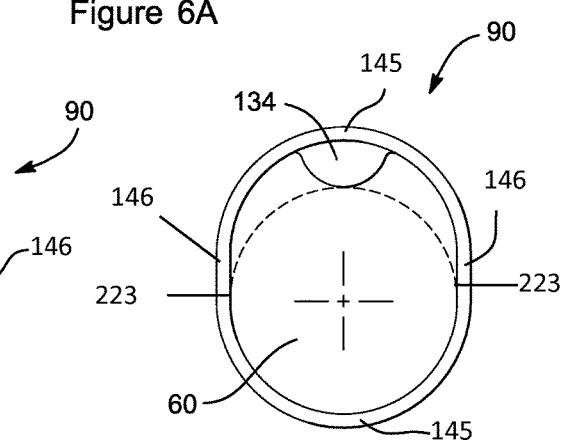
FIG. 6C illustrates an end view of a sheath including an endoscope.

FIG. 6C illustrates an end view of a sheath 90, including two opposing circular segments 145 that are connected together by tangent lines 147. One of the circular segments 145 includes a dimple 134 that offsets the endoscope 60 within the sheath 90. The endoscope 60 contacts the tangent lines 147 at a contact location 223, which is also a location where the tangents segments 146 are tangent to the endoscope 60. Each of the tangent segments 146 are also tangent with each of the circular segments 145.

Figure 7:
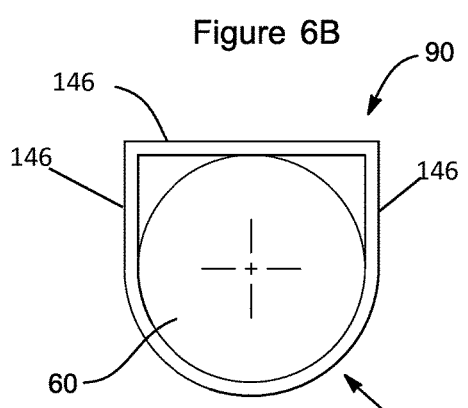
FIG. 7 illustrates an example of an end view of a sheath including one flat wall.

FIG. 7 illustrates a sheath 90 including a tangent segment 146 connected to a circular portion 142. An outer wall of the endoscope 60 is in contact with the circular portion 142 along it perimeter and the endoscope 60 is in contact with tangent portions 146 of the circular portion 142 at contact locations 223. The vertical tangent portions 146 are tangent to the endoscope 60 and are contiguous with the circular portion 142.

Figure 8:
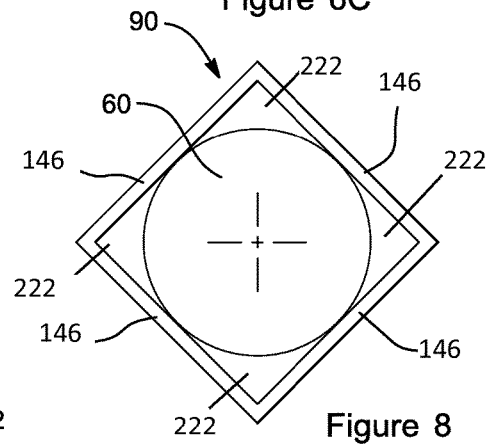
FIG. 8 illustrates an end view of a sheath have a plurality of flat walls.

FIG. 8 illustrates a sheath 90 including four tangent segments 146 forming a generally square perimeter. The endoscope 60 is in contact at a point with each of the tangent lines 147 forming gaps 222 past the endoscope 60.

Figure 9A:
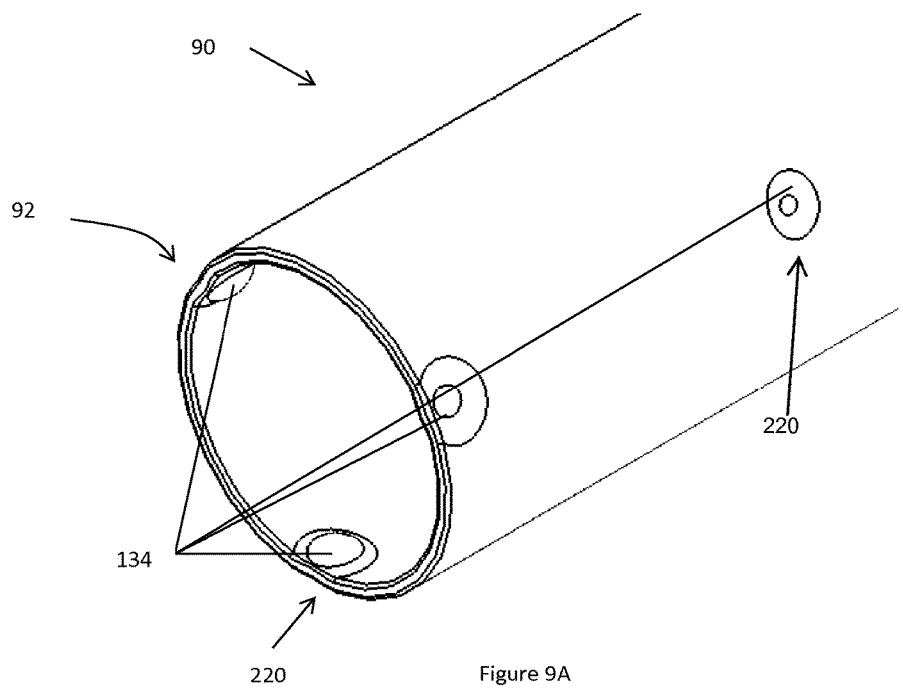
FIG. 9A illustrates a perspective view of a sheath including a plurality of positioning devices that are aligned.

FIG. 9A illustrates a perspective view of a sheath 90. The sheath includes a plurality of positioning devices 220. The positioning devices 220 are configures as dimples 134 with a set of three dimples located at the distal end 92 and a set of three dimples 134 at a location proximal of the distal end 92.

Figure 9B:
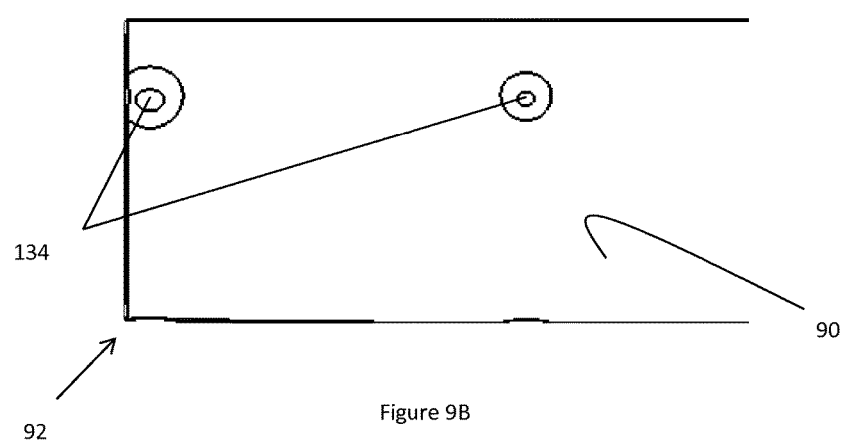
FIG. 9B illustrates a side view of the sheath of FIG. 9A.

FIG. 9B illustrates a side view of the sheath 90 of FIG. 9A. The sheath 90 has a first set of dimples 134 at the distal end and a second set of dimples 134 located on the proximal side of the first set so that the endoscope (not shown) forms an annular gap along its length.

Figure 9C:
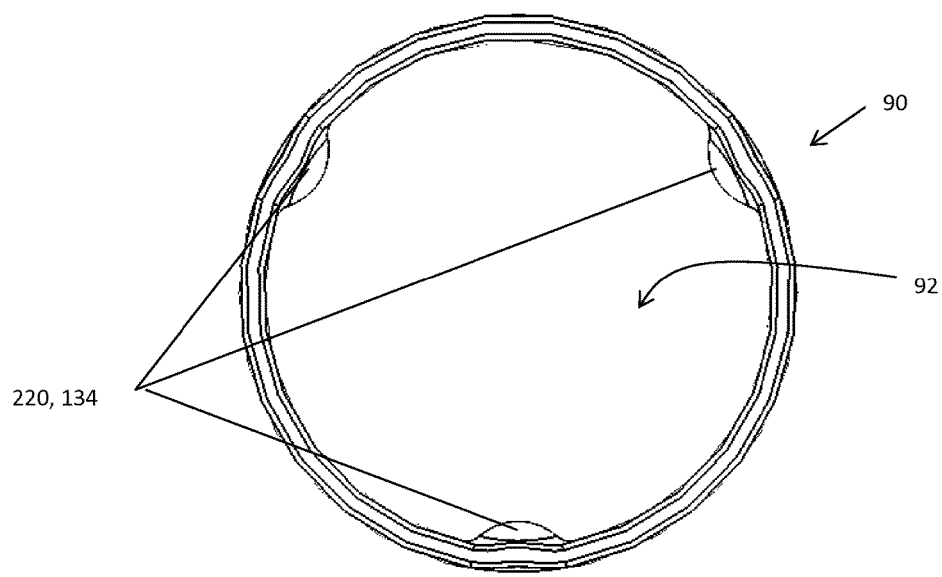
FIG. 9C illustrates an end view of the sheath of FIG. 9A

FIG. 9C illustrates an end view of the distal end 92 of the sheath 90 of FIG. 9A. The sheath 90 includes a three positioning devices 220 that are configured as dimples 134 equally spaced so that when an endoscope (not shown) is placed in the sheath 90 an equally sized annular gap is created around the endoscope.

FIG. 10A illustrates a perspective view of a sheath 90 having two sets of positioning devices 220. The first set of positioning devices 220 is located at the distal end 92 and is a set of pins 224 that create a distal end stop for an endoscope (not shown). The second set of positioning devices 220 which are located towards the proximal end relative to the first set of positioning devices 220 are configures as a plurality of dimples 134 that are located around the inside of the sheath 90.

FIG. 10B illustrates the sheath 90 from the distal end 92. The pins 224 are offset from the dimples 134 and the dimples 134 are equally spaced apart around the sheath 90.

FIG. 10C illustrates a view of the sheath 90 from a proximal end looking along line 10C-10C towards the distal end. The sheath 90 includes an endoscope 60 that is in contact with the pins 224 located on opposing sides of the sheath 90 so that the endoscope 60 is prevented from moving axially towards the distal end. The sheath 90 includes three dimples 134 that are spaced apart forming a gap 222 that is annular round the outside of the endoscope 60.

Figure 11C:
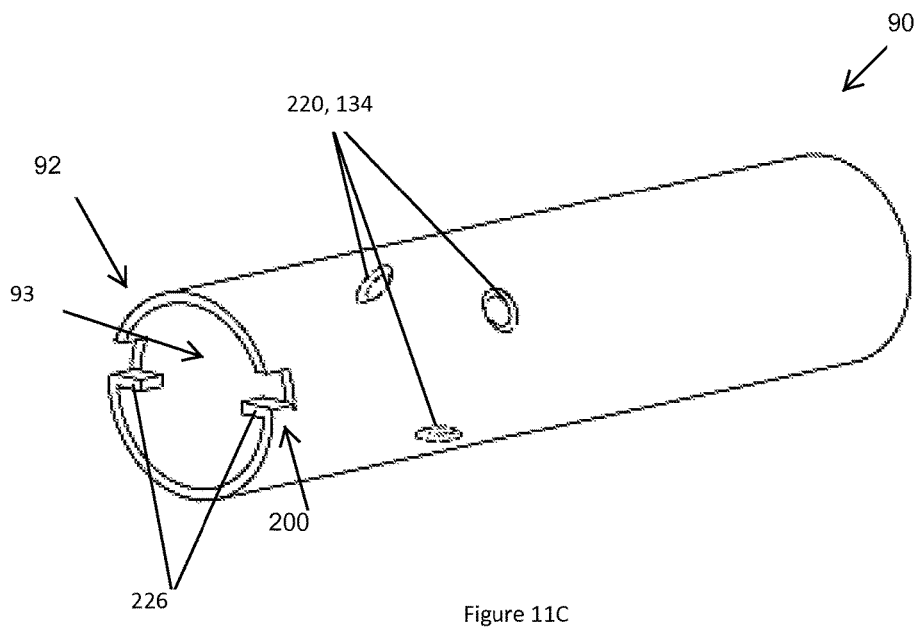
FIG. 11C illustrates a perspective view of a sheath having two different positioning devices.
Figure 11A:
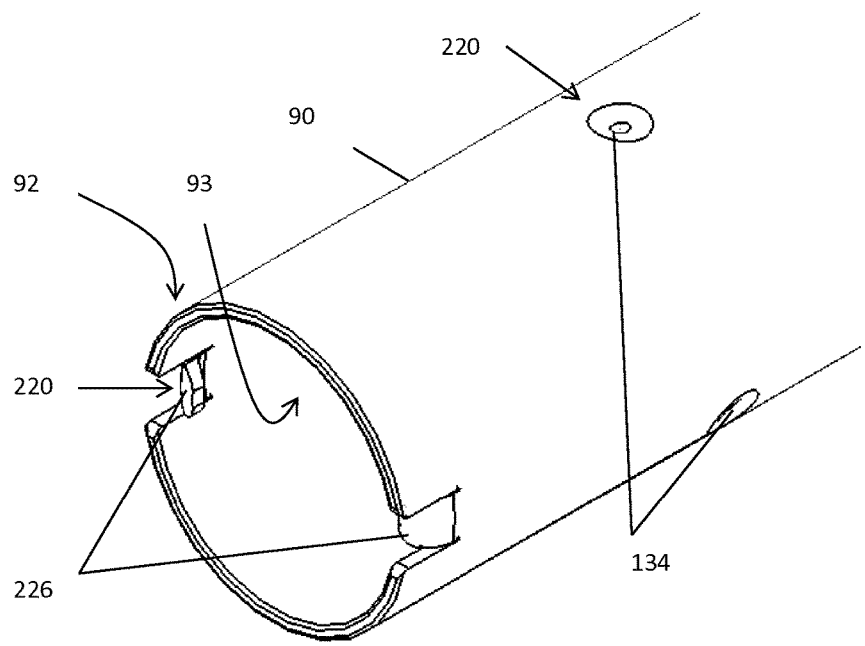
FIG. 11A illustrates a perspective view of a sheath having a plurality of two different positioning devices that are off set.

FIG. 11A illustrates a perspective view of a sheath 90 having an opening 93 at the end of the sheath 90 (i.e., a 0 degree sheath). The sheath 90 includes two sets of positioning devices 220. The first set of positioning devices 220 are crimps 226 that are located at the distal end 92. The second set of positioning devices 220 are dimples 134 that are located proximal of the distal end 92.

Figure 11B:
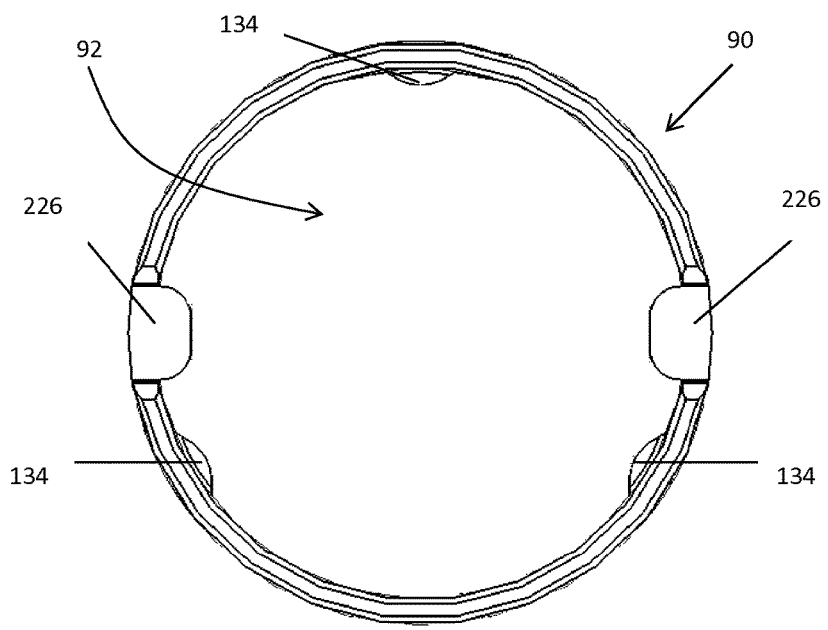
FIG. 11B illustrates an end view of the sheath of FIG. 11A.

FIG. 11B illustrates a view of the distal end 92 of the sheath 90. The sheath 90 includes a pair of opposing crimps 226 that prevent an endoscope (not shown) from extending out the distal end of the sheath 90. The sheath 90 also includes dimples 134 spaced around the sheath 90 and rotationally offset from the crimps 226 so that the endoscope (not shown) is positioned within the sheath 90.

FIG. 11C illustrates a perspective view of a sheath 90 including two sets of positioning devices 220. A first set of positioning devices 220 are configured as crimps 226 at the distal end 92 with the crimps 226 extending inward towards each other within the opening 93 of the sheath 90. A second set of positioning devices 220 are located proximal of the first set of positioning devices 220 and the second set are configured as dimples 134 for that are equally spaced apart around a circumference of the cylindrical sheath 90.

Figure 12A:
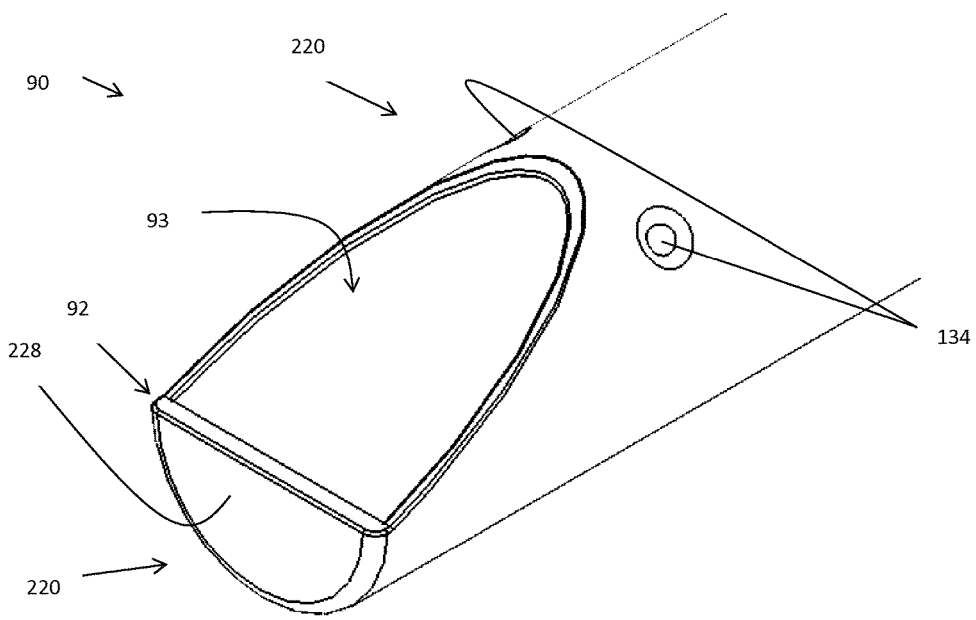
FIG. 12A illustrates a perspective view of an angled sheath having a plurality of positioning devices.

FIG. 12A illustrates an angled sheath 90 having an opening 93 on the side of the sheath 90 (i.e., a 70 degree sheath). The angled sheath 90 includes a positioning device 220 that is an end stop 228 and prevents movement of an endoscope (not shown) within the sheath towards the distal end 92. The angled sheath 90 further includes positioning devices 220 that are configured as dimples 134. The dimples 134 as shown are located on a single side of the sheath 90 and locate the endoscope (not shown) so that the endoscope is positioned against one side of the sheath 90 preventing the flow of fluid through a portion of the sheath 90 and moving the fluid so that all of the fluid moves through a portion of the sheath 90 positioned relative to the dimples 134.

Figure 12B:
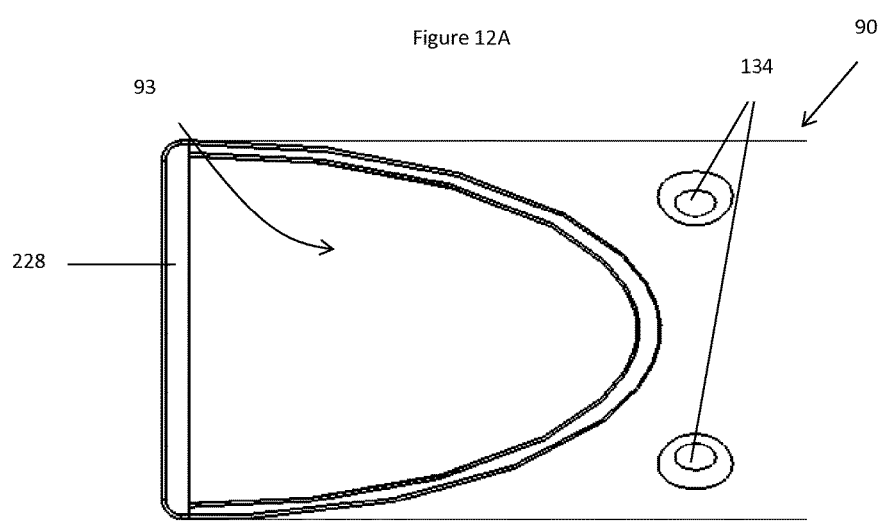
FIG. 12B illustrates a top view of the sheath of FIG. 12A.

FIG. 12B illustrates a top view of a sheath 90. The opening 93 is in the side of the sheath 90 and terminates at an end stop 228 that prevents an endoscope (not shown) from moving axially towards a distal end. A pair of dimples 134 are spaced apart and located on the side of the sheath 90 relative to the opening 93 so that fluid during an application cycle is moved across the endoscope cleaning its lens, imaging device, or both.

Figure 12C:
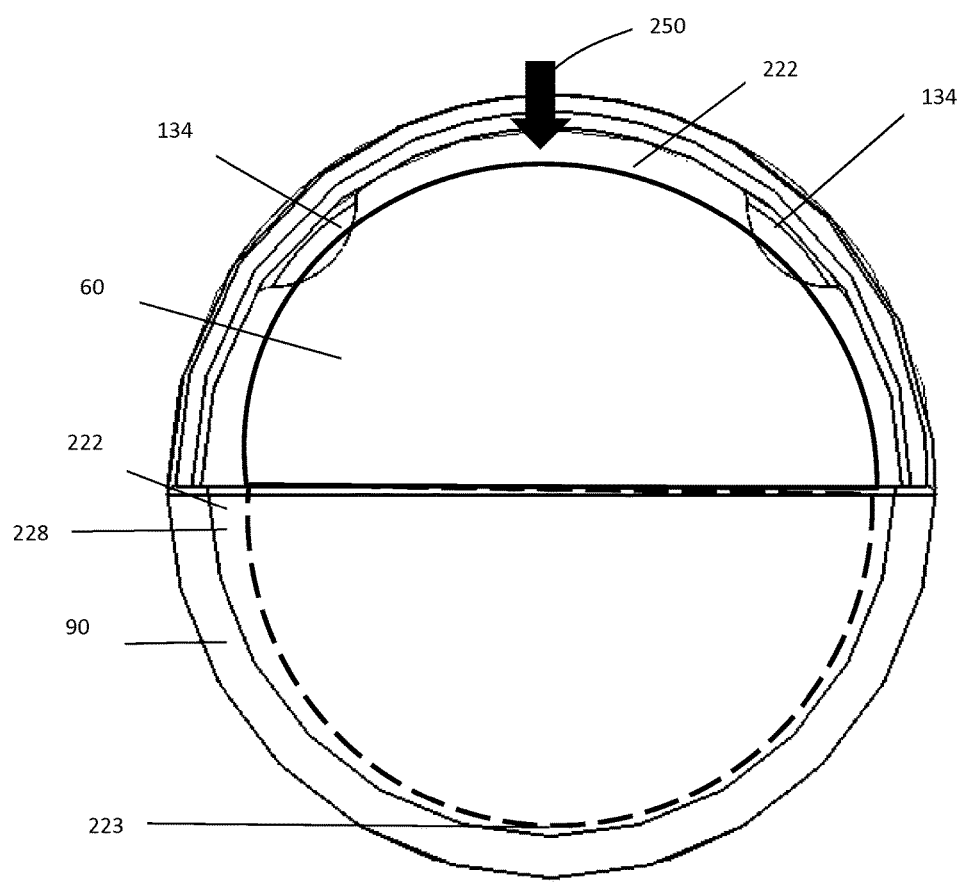
FIG. 12C illustrates an end view of the sheath of FIG. 12A.

FIG. 12C illustrates an end view of the sheath 90 of FIG. 12C including an endoscope 60 extending through the sheath 90. The endoscope 60 is in contact with an end stop 228, visible through a gap 222 and is shown in transparent, so that the contact location 223 between the endoscope 60 and the sheath 90 are in contact. The dimples 134 moves the endoscope 60 in the direction 250 so that a gap 222 is created between the endoscope 60 and a sheath 90 on a top side of the sheath 90 so that fluid can flow through gap 22, and a contact location 223 is formed between the endoscope 60 and the sheath 90 so that fluid flow is prevented.

Figure 13:
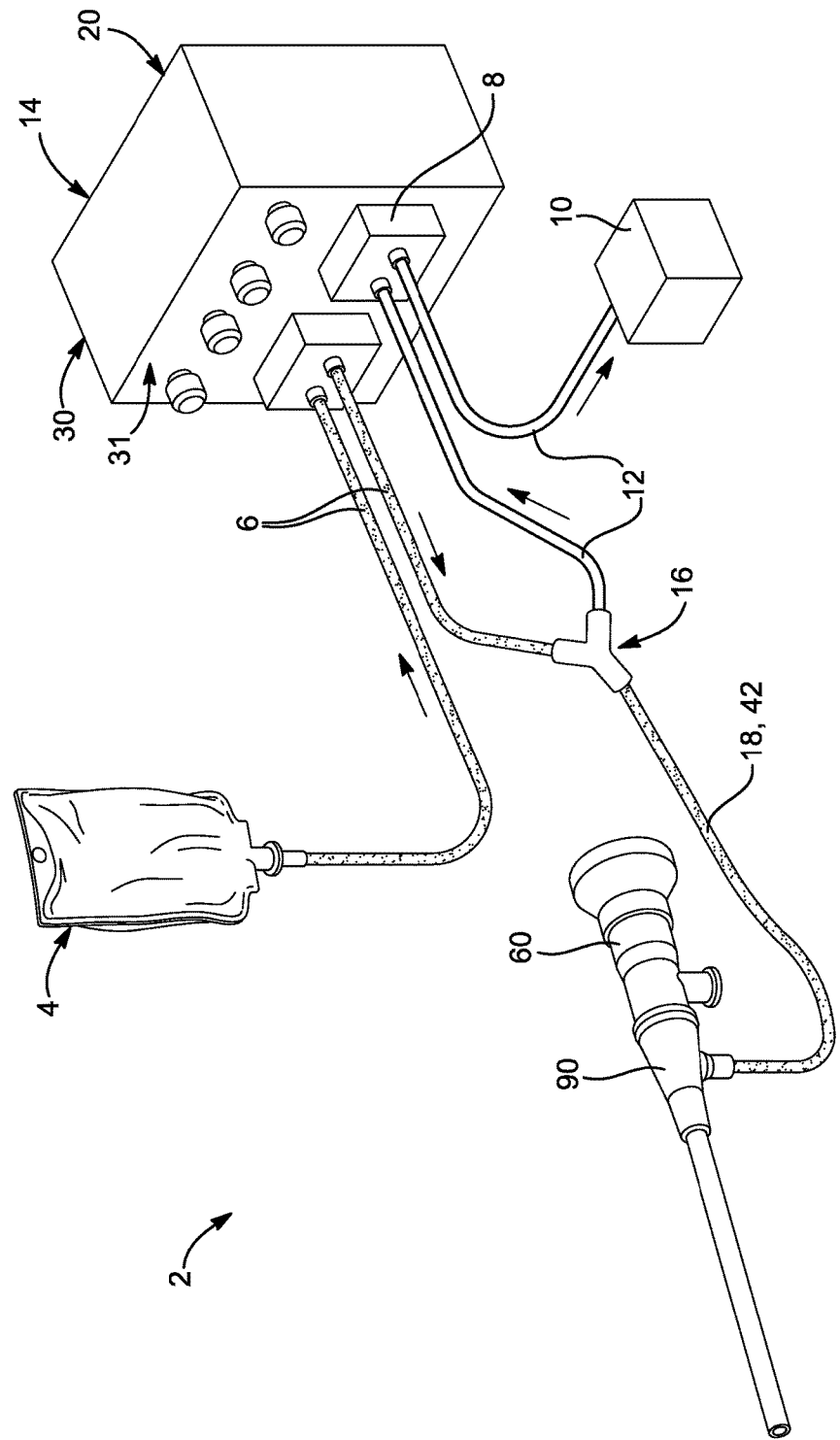
FIG. 13 illustrates a system including the sheath of the teachings herein.

FIG. 13 illustrates an endoscope cleaning system 2. The endoscope cleaning system 2 includes an irrigation source 4 connected to an irrigation line 6 that is connected to a control module 30 that includes a pump 14 for controlling flow of irrigation fluid between the irrigation source 4 and a sheath 90. The control module 30 includes a power source 20 and a controller and/or microprocessor (not shown) that is in communication with a user interface 31 for controlling the control module 30. The system 2 includes a suction source 10 that is connected to the control module 30. The control module 30 includes a valve 8 in the suction line that is connected to a sheath 90, which receives a portion of an endoscope. The valve 8 for controls suction between the suction source 10 and the sheath 90 so that suction may be turned off during all or portion of the application cycle of the irrigation fluid. The irrigation line 6 and the suction line 12 are connected together at a common fitting 16 that connects the irrigation line 6 and the suction line 12 to a common line 18/delivery line 42 for supplying a fluid or suction to the sheath 90 for cleaning an endoscope (not shown).

Figure 14:
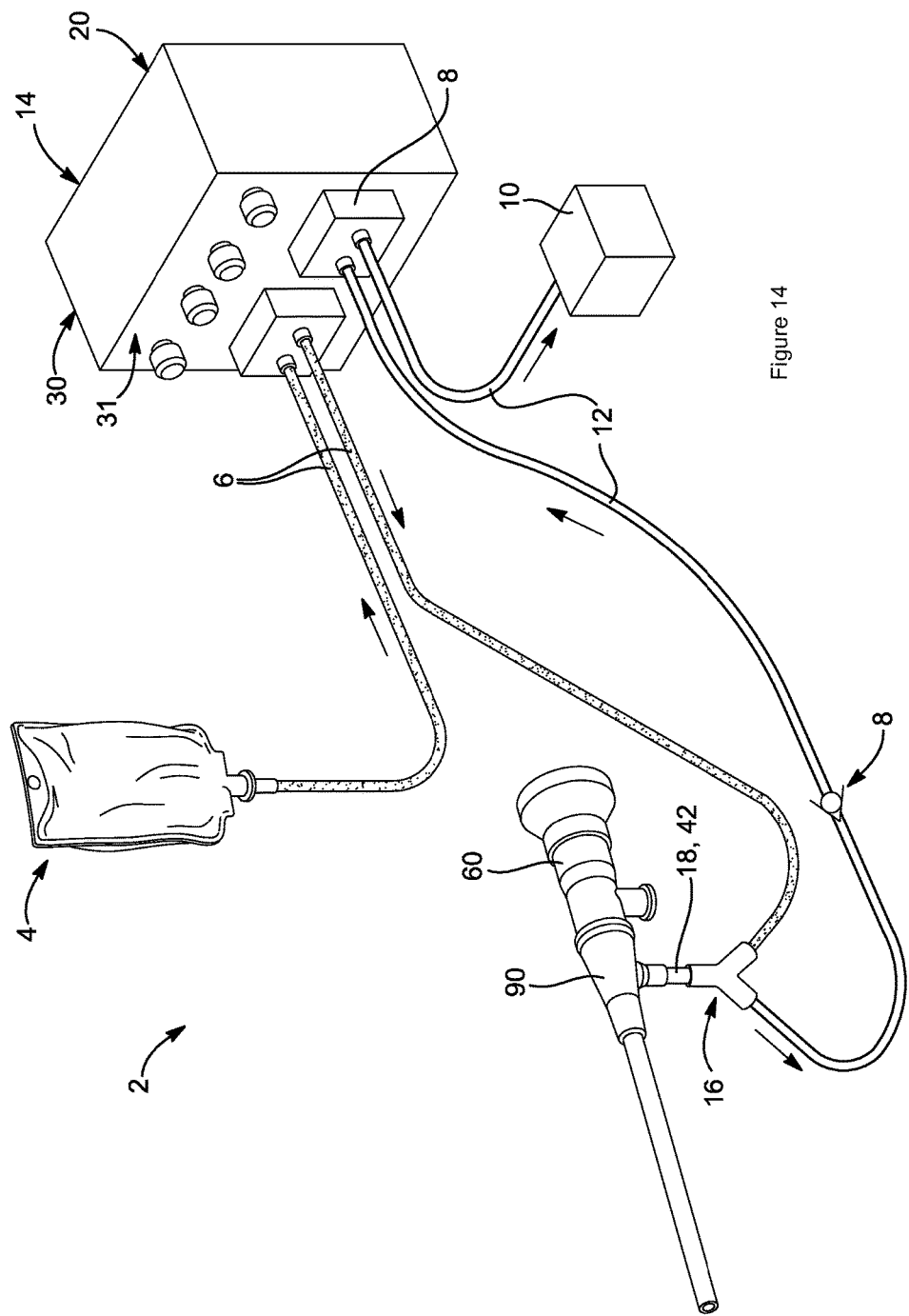
FIG. 14 illustrates another system including the sheath of the teachings herein.

FIG. 14 illustrates a control module 30 that includes a pump 14, a power source 20, a user interface 31, and one or more valves 8. The irrigation source 4 is gravity fed into the pump 14 and then the pump 14 sends fluid through the irrigation line 6 to the sheath 90 so that the sheath 90 washes the endoscope 60. The suction source 10 is connected to a valve 8 of the control module 30 that controls suction being drawn through the suction lines 12. Both the irrigation lines 6 and the suction lines 12 are connected to a common fitting 16 and a single common line 18/delivery line 42 extend from the common fitting 16 to the sheath 90. The suction line 12 may include a valve 8 that is a passive check valve to prevent irrigation fluid from being forced into the suction line.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. An endoscope sheath comprising:
a proximal end;
a distal end having a distal end region;
a surface extending between and connecting the proximal end and the distal end; and
a plurality of positioning devices located along the surface;
wherein the endoscope sheath is configured to:
  (1) receive all or a portion of an endoscope having a cylindrical end, and
  (2) provide a conduit for communicating fluid between the proximal end of the endoscope sheath and the distal end of the endoscope sheath when the endoscope is inserted inside the sheath;
wherein the distal end region of the endoscope sheath includes the plurality of positioning devices that secure the cylindrical end of the endoscope against a portion of an inner wall of the surface extending between the proximal end and the distal end so that a fluid barrier is created between the cylindrical end of the endoscope and the portion of the inner wall, wherein the plurality of positioning devices are two or more hemispherical dimples that displace the cylindrical end of the endoscope against the portion of the inner wall, wherein the endoscope sheath includes an end stop, the end stop is located at the distal end of the endoscope sheath, the end stop prevents movement of the endoscope past the distal end of the endoscope sheath when the cylindrical end of the endoscope is received in the endoscope sheath;

wherein the end stop is a planar wall that is located at the distal-most end of the sheath, the planar wall extends perpendicularly to a longitudinal axis of the endoscope sheath, the end stop extends from a first side of the surface towards a second opposing side of the surface and terminates at a straight edge that is located at the distal-most end of the sheath and is located between the first side of the surface and the second opposing side of the surface, and wherein the endoscope sheath includes an opening extending at an angle from the straight edge of the end stop at the distal-most end of the endoscope sheath towards the second opposing side of the surface and towards the proximal end of the endoscope sheath, wherein a full circumferential edge of the opening lies on a single plane, and wherein the two or more hemispherical dimples are located proximate to the opening on the second opposing side and displace the endoscope from the second opposing side of the surface to the first side of the surface so that the conduit is created at the second opposing side so that irrigation fluid is moved over a viewing lens of the endoscope and the angle of the opening substantially matches an angle of the viewing lens.

2. The endoscope sheath of claim 1, wherein the portion of the inner wall is circular and the inner wall has an arc length in contact with the endoscope of about 30 degrees or more.

3. The endoscope sheath of claim 1, wherein the conduit is defined between two of the dimples, the cylindrical end of the endoscope and another portion of the inner wall.

* * * * *